(12) United States Patent
Hudson et al.

(10) Patent No.: US 7,407,949 B2
(45) Date of Patent: *Aug. 5, 2008

(54) BENZAMIDE DERIVATIVES AS OXYTOCIN AGONISTS AND VASOPRESSIN ANTAGONISTS

(75) Inventors: Peter Hudson, Copenhagen S (DK); Andrzej Roman Batt, Southampton (GB); Celine Marguerite Simone Heeney, Southampton (GB); Andrew John Baxter, Romsey Hants (GB); Michael Bryan Roe, Southampton (GB); Peter Andrew Robson, Hampshire (GB)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/541,460

(22) PCT Filed: Feb. 12, 2004

(86) PCT No.: PCT/EP2004/001304

§ 371 (c)(1),
(2), (4) Date: Mar. 6, 2006

(87) PCT Pub. No.: WO2004/072083

PCT Pub. Date: Aug. 26, 2004

(65) Prior Publication Data

US 2006/0166971 A1    Jul. 27, 2006

(30) Foreign Application Priority Data

Feb. 14, 2003 (EP) .................. 03003394

(51) Int. Cl.
  *A61P 15/00* (2006.01)
  *A61K 31/5517* (2006.01)
  *C07D 498/04* (2006.01)
  *C07D 471/04* (2006.01)
  *C07D 471/14* (2006.01)
  *C07D 487/04* (2006.01)
  *C07D 495/04* (2006.01)

(52) U.S. Cl. .............. 514/211.08; 514/211.1; 514/211.12; 514/211.14; 514/215; 514/217; 514/220; 540/545; 540/547; 540/548; 540/554; 540/557; 540/558; 540/560; 540/561; 540/562; 540/577; 540/578; 540/586

(58) Field of Classification Search ............ 514/211.08, 514/211.1, 211.12, 211.14, 215, 217, 220; 540/545, 547, 548, 554, 557, 558, 560, 561, 540/562, 577, 578, 586
See application file for complete search history.

(56) References Cited

U.S. PATENT DOCUMENTS 5,760,031 A    6/1998 Albright ............. 514/215

FOREIGN PATENT DOCUMENTS

| WO | WO 02/083682 A | 10/2002 |
| WO | WO 03/000692 A | 1/2003 |
| WO | WO 03/016316 A | 2/2003 |

OTHER PUBLICATIONS

International Search Report of PCT/EP2004/001304.
Thomas Bossmar et al., "Effects of SR 49059, an orally active V1a vasopressin receptor antagonist, on vasopressin-induced uterine contractions", British Journal of Obstetrics & Gynaecology, Apr. 1997, vol. 104, pp. 471-477.

(Continued)

*Primary Examiner*—Brenda L Coleman
(74) *Attorney, Agent, or Firm*—Foley & Lardner

(57) ABSTRACT

Novel compounds according to general formula 1, wherein $G^1$ is $NR^5R^6$ or a fused polycyclic group that are specific OT receptor agonists and/or $V_{1a}$ receptor antagonists. Pharmaceutical compositions comprising such compounds are useful in the treatment of, inter alia, primary dysmenorrhoea.

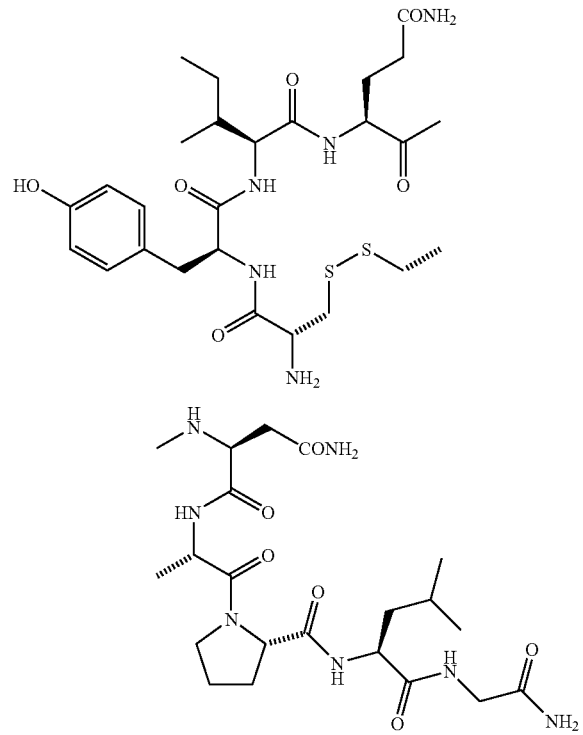

7 Claims, No Drawings

OTHER PUBLICATIONS

R. Brouard et al., "Effect of SR49059 an orally active $V_{1a}$ vasopressin receptor antagonist, in the prevention of dysmenorrhoea", British Journal of Obstetrics & Gynaecology, May 2000, vol. 107, pp. 614-619.

Venkatesan Aranapakam et al., '4,10-Dihydro-5H-Thieno[3,2-c][1]Benzazepine Derivatives and 9,10-Dihydro-4H-Thieno[2,3-C][1]Benzazepine Derivatives as Orally Active Arginine Vasopressin Receptor Agonists, Bioorganic & Medicinal Chemistry Letters 9 (1999) pp. 1733-1736.

M. Artico et al., "Ricerche su Sostanze ad Attivita Antiblastica", II Fármaco., Ed. Sc. vol. 24, No. 3, pp. 276-284, Mar. 1969.

F. Chimenti et al., "Ricerche su Sostanze ad Attivita Antiblastica", II Fármaco, Ed. Sc. vol. 32, No. 5, pp. 339-347, May 1977.

Jiban K. Chakrabarti et al., "4-piperazinyl-10H-thieno[2,3-b][1,5]benzodiazepines as Potential Neuroleptics", J. Med. Chem. 1980, 23, pp. 878-884.

Jiban K. Charabarti et al., "10-Piperazinyl-4H-thieno[3,2-b][1,5]- and-[3,4-b][1,5]benzodiazepines as Potential Neuroleptics", J. Med. Chem. 1980, 23, pp. 884-889.

Jiban K. Charabarti et al., Synthesis and Pharmacological Evaluation of a Series of 4-Piperazinylpyrazolo[3,4-b]- and-[4,3-b][1,5]benzodiazepines as Potential Anxiolytics, J. Med. Chem. 1989, 32, pp. 2573-2582.

Alba Chimirri et al., "Annelated 1,5-Benzodiazepines. Part I. Three, Four, and Five Membered Rings", Heterocycles, vol. 36, No. 3, 1993, pp. 601-637.

Gary L. Gunewald et al., "Effect of Ring Size or an Additional Heteroatom on the Potency and Selectivity of Bicyclic Benzylamine-Type Inhibitors of Phenylethanolamine N-Methyltransferase", J. Med. Chem. 1996, 39, 3539-3546.

Janice M. Klunder et al., "Novel Non-Nucleoside Inhibitors of HIV-1 Reverse Transcriptase. 2. Tricyclic Pyridobenzoxazepinones and Dibenzoxazepinones", J. Med. Chem., 1992, 35, pp. 1887-1897.

Jean-Françoise F. Liégeois et al., "Pyridobenzoxazepine and Pyridobenzothiazepine Derivates as Potential Central Nervous System Agents: Synthesis and Neurochemical Study", J. Med. Chem. 1994, 37, pp. 519-525.

Timothy O. Olagbermiro et al., "Alkylation and an Unusual Reductive Ring Opening of Some Thieno[3,4-b][1,5]benzoxazepin-10-ones", Department of Chemistry, Bayero University, Kano, Nigeria, vol. 19, Nov.-Dec. 1982, pp. 1501-1504.

William B. Wright Jr. et al., "Derivatives of 11-(1-Piperazinyl)-5H-pyrrolo[2,1-c][1,4]benzodiazepine as Central Nervous Systems Agents", J. Med. Chem. 1980, 23, pp. 462-465.

Satoru Sasatani et al., "Diisobutylaluminum Hydride a Novel Reagent for the Reduction of Oximes", Tetrahedron Letters, vol. 24, No. 43, pp. 4711-4712, 1983.

BENZAMIDE DERIVATIVES AS OXYTOCIN AGONISTS AND VASOPRESSIN ANTAGONISTS

FIELD OF THE INVENTION

The present invention relates to novel non-peptide oxytocin agonists and to pharmaceutical compositions comprising such compounds. The present invention also relates to the use of non-peptide oxytocin agonists for the treatment of certain physiological disorders, such as erectile dysfunction and primary dysmenorrhoea.

BACKGROUND

Neurophyseal Hormones

The neurophyseal hormones oxytocin (OT) and vasopressin (VP) are cyclic nonapeptides secreted by the posterior pituitary gland. The structure of oxytocin is shown below.

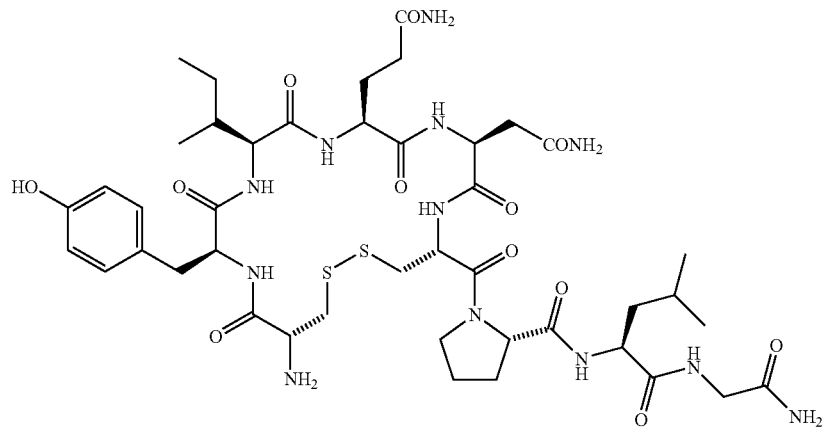

Oxytocin-cyclo$^{1,6}$-Cys-Tyr-Ile-Gln-Asn-Cys-Pro-Leu-Gly-NH$_2$

Vasopressin differs from oxytocin in that it has phenylalanine at position 3 in place of isoleucine and arginine at position 8 in place of leucine. Both hormones are synthesised in vivo as larger precursors, neurophysins, which are subject to post-translational processing to release the mature peptides. OT and VP act through a family of heptahelical receptors. Only one OT receptor has so far been well characterised, while three VP receptors are known. These are designated the $V_{1a}$, $V_{1b}$ and $V_2$ receptors.

The first target organs to be identified for OT were the uterus, where it is implicated in the onset and progress of labour, and mammary glands, where it is involved in the regulation of milk expression. Other organs also express OT receptors, and it is clear that OT has a range of physiological roles that have not been fully elaborated yet. In particular, it has been suggested that OT acting in the CNS is involved in the erectile response in males, and in the regulation of female sexual arousal. For example, OT is erectogenic when administered i.c.v. to male rats. It also has erectogenic activity when given i.v., but the doses required are up to two orders of magnitude greater, which is consistent with a central mode of action.

Vasopressin acts on the blood vessels, where it is a potent vasoconstrictor, and on the kidneys, where it promotes water reuptake leading to an antidiuretic effect.

Oxytocin Agonists and Antagonists

A number of peptide analogues of OT are known in the literature. These include both agonists and antagonists. OT and its agonists are used, for example, to accelerate labour and to increase uterine muscle tone to control postpartum bleeding, and one antagonist, atosiban, has recently been registered as a treatment for pre-term labour. However, the peptidic nature of these compounds means that they are not likely to be bioavailable after oral dosing or to cross efficiently into the CNS. In order to get drugs that can be given orally and to be able to exploit the central effects of OT, attention has increasingly turned to non-peptides. As a result, there are many publications describing non-peptide OT antagonists in early-stage development. So far, however, there have been no reports of non-peptide OT agonists. This is not unexpected, as it is generally held that it is easier to find a receptor antagonist than an agonist.

So there remains a need for non-peptide OT receptor agonists. Such compounds should preferably be selective for the OT receptor over the VP receptors. They could be expected to show therapeutic utility in male and female sexual dysfunction, particularly male erectile dysfunction, in promoting labour, in controlling post-partum bleeding, in increasing milk let-down as well as a number of other indications.

Vasopresin Agonists and Antagonists

The $V_{1a}$ receptor is normally acted upon by the endogenous agonist ligand, arginine vasopressin (AVP). AVP also acts on the $V_{1b}$ and $V_2$ receptors. It exerts a variety of biological effects in mammals including regulation of water and solute excretion by the kidney. AVP is structurally related to OT.

The $V_{1a}$, $V_{1b}$, and $V_2$, as well as the OT receptors, are members of the super-family of seven transmembrane receptors known as G-protein coupled receptors. The $V_{1a}$ receptor mediates phospholipase C activation and intracellular calcium mobilisation. Localisation of the receptors includes blood platelets, blood vessels, hepatocytes, brain and uterus-cervix. Thus a $V_{1a}$ antagonist may have effects on any or all of these tissues. For example, selective $V_{1a}$ antagonists have been cited as having clinical utility in primary dysmenorrhoea, pre-term labour, hypertension, Raynauld's disease, brain oedema, motion sickness, small cell lung cancer, depression, anxiety, hyponatremia, liver cirrhosis and congestive heart failure.

With respect to primary dysmenorrhoea it has been proposed that myometrial activity is markedly increased in women with primary dysmenorrhoea during menstruation. It is proposed that the myometrial ischemia caused by increased uterine contractility might explain the menstrual pain. Furthermore, on the first day of menstruation, higher plasma concentrations of vasopressin have been measured in dysmenorrhoeal women than in controls.

In healthy women without dysmenotrrhoea, intravenous infusion of lysine-vasopressin resulted in decreased uterine blood flow, increased uterine contractility and slight to moderate like-like pain, these effects being inhibited by a selective human $V_{1a}$ receptor antagonist. (Bossmar T; Brouard R; Doberl A; Akerlund M, Department of Obstetrics and Gynaecology, University Hospital of Lund, Sweden BRITISH JOURNAL OF OBSTETRICS AND GYNAECOLOGY (1997 April), 104(4), 471-7.). Also, it is known that vasopressin contracts human uterine arteries in a dose-dependent and $V_{1a}$-mediated fashion.

The above evidence suggests that a $V_{1a}$ antagonist would be an appropriate and effective treatment for primary dysmenorrhoea. Further evidence is taken from the clinical study carried out on the selective $V_{1a}$ antagonist SR49059 ("Effect of SR49059, an orally active $V_{1a}$ vasopressin receptor antagonist, in the prevention of dysmenorrhea". Brouard, R.; Bossmar, T.; Fournie-Lloret, D.; Chassard, D.; Akerlund, M. Sanofi Recherche, Clinical Development, Paris, Fr. BJOG (2000), 107(5), 614-619.). It was found that there was a dose-related decrease in pain and a dose-related decrease in the amount of additional pain-killer taken compared to patients taking placebo.

SUMMARY OF THE INVENTION

The present invention is based on a series of potent and specific OT receptor agonists (herein also called OT agonists) and/or VP receptor antagonists (herein also called VP antagonists) according to general formula 1:

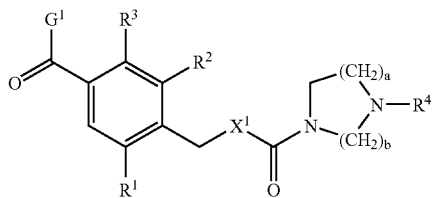

1 wherein $G^1$ is a group according to general formula 2, 3, 4, 5, 6 or 7:

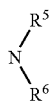

2

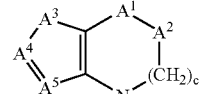

3

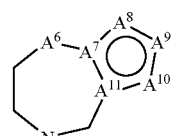

4

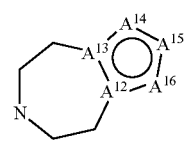

5

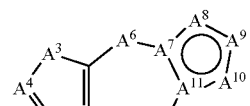

6

7 wherein:
$A^1$ is $CH_2$, CH(OH), NH, N-alkyl, O or S;
$A^2$ is $CH_2$, CH(OH), C(=O) or NH;
$A^3$ is S, NH, N-alkyl, —CH=CH— or —CH=N—;
$A^4$ and $A^5$ are each CH or N;
$A^6$ is $CH_2$, NH, N-alkyl or O;
$A^7$ and $A^{11}$ are C or N;
$A^8$ and $A^9$ are CH, N, NH, —N(CH$_2$)$_d$R$^7$ or S;
$A^{10}$ is —CH=CH—, CH, N, NH, N—(CH$_2$)$_d$—R$^7$ or S;
$A^{12}$ and $A^{13}$ are N or C and
$A^{14}$, $A^{15}$ and $A^{16}$ are NH, N—CH$_3$, S, N or CH, provided that not more than one of $A^8$, $A^9$ and $A^{10}$ is NH, N—(CH$^2$)$_d$—R$^7$ or S; that $A^7$ and $A^{11}$ are not both simultaneously N; that neither $A^7$ nor $A^{11}$ is N if one of $A^8$, $A^9$ and $A^{10}$ is NH, N—(CH$_2$)$_d$—R$^7$ or S; that if $A^{10}$ is not —CH=CH— then one of $A^8$, $A^9$ and $A^{10}$ is NH, N—(CH$_2$)$_d$—R$^7$ or S or one of $A^7$ and $A^{11}$ is N; that not more than one of $A^{14}$, $A^{15}$ and $A^{16}$ is NH, N—CH$_3$ or S; that $A^{12}$ and $A^{13}$ are not both simultaneously N; that if one of $A^{14}$, $A^{15}$ and $A^{16}$ is NH, N—CH$_3$ or S then $A^{12}$ and $A^{13}$ are both C; and that one of $A^{14}$, $A^{15}$ and $A^{16}$ is NH, N—CH$_3$ or S or one of $A^{12}$ and $A^{13}$ is N;

$X^1$ is O or NH;
$R^1$, $R^2$ and $R^3$ are each H, alkyl, O-alkyl, F, Cl or Br;
$R^4$ is H, alkyl, optionally substituted-phenyl, pyridyl, thienyl or furyl, or is —(CH$_2$)$_e$—R$^8$:
$R^5$ and $R^6$ are each, independently of each other, alkyl, Ar or —(CH$_2$)$_f$—Ar, where Ar is optionally substituted phenyl or thienyl;
$R^7$ and $R^8$ are each, independently of each other, H, alkyl, optionally substituted phenyl, pyridyl, thienyl or furyl, F, OH, O-alkyl, S-alkyl, O-acyl, NH$_2$, NH-alkyl, N(alkyl)$_2$, NH-acyl, N(alkyl)-acyl, CO$_2$H, CO$_2$-alkyl, CONH$_2$, CONH-alkyl, CON(alkyl)$_2$, CN or CF$_3$;

a is 1 or 2, b is 1, 2 or 3, c is 1 or 2, d is 1, 2 or 3; e is 1, 2 or 3 and f is 1, 2 or 3.

According to a first aspect, the present invention relates to novel OT agonists and/or VP antagonists, and in particular specific antagonists of the $V_{1a}$ receptor, and pharmaceutically acceptable salts thereof.

According to a second aspect, the present invention relates to pharmaceutical compositions comprising these novel compounds, which compositions are useful for the treatment of, inter alia, male erectile dysfunction and primary dysmenorrhoea.

According to a third aspect, the present invention relates to the use of these novel compounds for the manufacture of a pharmaceutical composition for the treatment of erectile dysfunction.

According to a fourth aspect, the present invention relates to the use of the compounds in the above mentioned series of potent and specific OT receptor agonists and/or VP receptor antagonists for the manufacture of a pharmaceutical composition for treatment of dysmenorrhoea.

According to further aspects, the present invention relates to the use of the above mentioned compounds and compositions in therapy and to therapeutic methods wherein the above mentioned compounds and compositions are used.

DETAILED DESCRIPTION OF THE INVENTION

Thus, according to the first aspect, the present invention relates to novel specific OT agonists and/or novel specific $V_{1a}$ antagonists. These compounds are benzyl carbamates and ureas having the general formula 1:

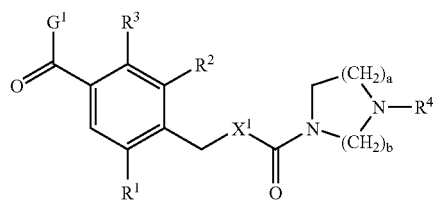

In this general formula the substituents $R^1$, $R^2$ and $R^3$ are, independently of each other, selected from hydrogen (H), alkyl groups, alkoxy (O-alkyl) groups, and the halogens fluorine (F), chlorine (Cl) and bromine (Br). Preferably, at least one of $R^1$, $R^2$ and $R^3$ is H and at least one is not H. More preferably, two of $R^1$, $R^2$ and $R^3$ are H, and the other is an alkyl group, an O-alkyl group or a halogen.

The linking group $X^1$ is selected from oxygen (O) and unsubstituted nitrogen (NH). Preferably, $X^1$ is NH.

The integer a may be 1 or 2, and the integer b may be 1, 2 or 3. Preferably a is 1 and b is 2 such that this ring is a piperazine.

The substituent $R^4$ is selected from H, alkyl groups, alkenyl groups, alkynyl groups, optionally substituted phenyl, optionally substituted thienyl, optionally substituted furyl, optionally substituted pyridyl, pyrrolyl, pyrazolyl, imidazolyl, oxazolyl, isoxazolyl, thiazolyl and isothiazolyl groups, a group —$(CH_2)_e R^8$, wherein e is 1, 2, 3 or 4, —$CH_2$—CH=CH—$CH_2$—$R^8$, —$CH_2$—C≡C—$CH_2$—$R^8$, —$(CH_2)_g$—CH(OH)—$(CH_2)_h$—$R^8$, wherein g and h are, independently of each other, 1 or 2, —$(CH^2)_i$—O—$(CH_2)_j$—$R^8$ wherein i and j are, independently of each other, 1 or 2, and

wherein $R^8$ is selected from H, F, $CF_3$, alkyl groups, alkenyl groups, alkynyl groups, acyl groups, O-alkyl groups, S-alkyl groups, O-acyl groups, hydroxyalkyl groups, amino groups such as $NH_2$, NH-alkyl, $N(alkyl)_2$, 1-pyrrolidinyl, 1-piperidinyl and 4-morpholinyl, NH-acyl, N(alkyl)-acyl, $CO_2H$, $CO_2$-alkyl, $CONH_2$, CONH-alkyl, $CON(alkyl)_2$, CN and optionally substituted phenyl, optionally substituted pyridyl, optionally substituted thienyl, optionally substituted furyl, optionally substituted pyrrolyl, optionally substituted pyrazolyl, optionally substituted imidazolyl, optionally substituted oxazolyl, optionally substituted isoxazolyl, optionally substituted thiazolyl and optionally substituted isothiazolyl groups. Suitable optional substituents for the phenyl, pyridyl, thienyl, furyl, pyrrolyl, pyrazolyl, imidazolyl, oxazolyl, isoxazolyl, thiazolyl and isothiazolyl groups in $R^4$ and $R^8$ include F, Cl, Br, $CF_3$, alkyl groups, OH, O-alkyl groups, hydroxyalkyl groups, amino groups such as $NH_2$, NH-alkyl and $N(alkyl)_2$, NH-acyl, N(alkyl)-acyl, $CO_2H$, $CO_2$-alkyl, $CONH_2$, CONH-alkyl, $CON(alkyl)_2$, oxadiazolyl, thiadiazolyl, CN and $NO_2$. The phenyl, pyridyl, thienyl furyl, pyrrolyl, pyrazolyl, imidazolyl, oxazolyl, isoxazolyl, thiazolyl or isothiazolyl group may have up to three such substituents which may be the same or different.

The group $G^1$ is a disubstituted nitrogen such that the $C(=O)$-$G^1$ bond is an amide bond. $G^1$ is selected from an acyclic group according to general formula 2, a fused bicyclic group according to general formulae 3, 4 and 5, and a fused tricyclic group according to general formulae 6 and 7.

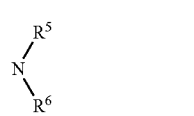

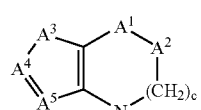

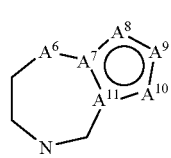

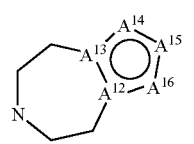

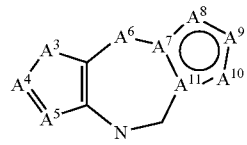

-continued

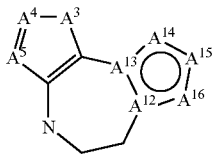

7

In general formula 2, $R^5$ and $R^6$ are, independently of each other, selected from alkyl, Ar and —$(CH_2)_f$—Ar, wherein f is 1, 2 or 3 and Ar is selected from optionally substituted thienyl and optionally substituted phenyl. Suitable substituents for the phenyl group are alkyl groups, OH, alkoxy groups, halogens, $NH_2$, NH-alkyl and $N(alkyl)_2$. The phenyl group may be substituted with up to three such substituents which may be the same or different.

In general formula 3, $A^1$ is selected from $CH_2$, CH(OH), NH, N-alkyl, O and S. $A^2$ is selected from $CH_2$, CH(OH), C(=O) and NH, and c is 1 or 2, preferably 2. It is preferred that when $A^2$ is NH then $A^1$ is $CH_2$. It is also preferred that when $A^2$ is C(=O) then $A^1$ is NH or N-alkyl.

In general formulae 3, 6 and 7, $A^3$ is selected from S, NH, N-alkyl, —CH=CH— and —CH=N— and $A^4$, and $A^5$ are each, independently of each other, selected from CH and N. In a preferred embodiment, $A^3$ is S and $A^4$ and $A^5$ are both CH, so as to form a thiophene ring. In another preferred embodiment, $A^3$ is —CH=CH— and $A^4$ and $A^5$ are both CH, so as to form a benzene ring. In another preferred embodiment, $A^3$ is —CH=N— and $A^4$ and $A^5$ are both CH, so as to form a pyridine ring. In another preferred embodiment, $A^3$ is —CH=CH—, $A^4$ is CH and $A^5$ is N, again so as to form a pyridine ring.

In general formulae 4 and 6, $A^6$ is selected from $CH_2$, NH, N-alkyl and O, $A^7$ and $A^{11}$ are, independently of each other, selected from C and N, $A^8$ and $A^9$ are, independently of each other, selected from CH, N, NH, N—$(CH_2)_d$—$R^7$ and S, and $A^{10}$ is selected from —CH=CH—, CH, N, NH, N—$(CH_2)_d$—$R^7$ and S, wherein d is 1, 2 or 3 and $R^7$ is selected from H, F, $CF_3$, alkyl groups, OH, O-alkyl groups, S-alkyl groups, O-acyl groups, amino groups such as $NH_2$, NH-alkyl and $N(alkyl)_2$, NH-acyl, N(alkyl)-acyl, $CO_2H$, $CO_2$-alkyl, $CONH_2$, CONH-alkyl, $CON(alkyl)_2$, CN and optionally substituted phenyl groups. Suitable optional substituents for the phenyl groups in $R^7$ include F, Cl, Br, $CF_3$, alkyl groups, O-alkyl groups, amino groups such as $NH_2$, NH-alkyl and $N(alkyl)_2$, NH-acyl, N(alkyl)-acyl, $CO_2H$, $CO_2$-alkyl, $CONH_2$, CONH-alkyl, $CON(alkyl)_2$, CN and $NO_2$. The phenyl group may have up to three such substituents which may be the same or different.

The ring constituted by $A^7$, $A^8$, $A^9$, $A^{10}$ and $A^{11}$ is aromatic, and accordingly the groups must satisfy certain requirements. When $A^{10}$ is —CH=CH— the ring is a six-membered ring. As such, it can only comprise atoms of the type. —C(R)= and —N=. Hence $A^7$ and $A^{11}$ must both be C and $A^8$ and $A^9$ must be either CH or N. When $A^{10}$ is not —CH=CH— then the ring is a five-membered ring. In this case one, and only one, of the atoms in the ring must be S or a trigonal nitrogen. In this context, a "trigonal nitrogen" is a nitrogen atom linked covalently to three different atoms. Two of these atoms are the immediate neighbours to the nitrogen atom in the five-membered ring. The third is a hydrogen, carbon or other atom linked to the five-membered ring. Thus it follows that, when $A^{10}$ is not —CH=CH— then one (and only one) of $A^7$, $A^8$,

8

$A^9$, $A^{10}$ and $A^{11}$ must be S or a trigonal nitrogen. Hence the selection of $A^7$, $A^8$, $A^9$, $A^{10}$ and $A^{11}$ is subject to the following restrictions.
1) If $A^{10}$ is not —CH=CH— then one of $A^8$, $A^9$ and $A^{10}$ is NH, N—$(CH_2)_d$—$R^7$ or S or one of $A^7$ and $A^{11}$ is N.
2) Not more than one of $A^8$, $A^9$ and $A^{10}$ may be NH, N—$(CH_2)_d$—$R^7$ or S.
3) $A^7$ and $A^{11}$ may not both simultaneously be N.
4) Neither $A^7$ nor $A^{11}$ may be N if one of $A^8$, $A^9$ and $A^{10}$ is NH, $N(CH_2)R^7$ or S In a preferred embodiment, $A^6$ is NH. In another preferred embodiment, $A^8$ is NH or N—$(CH_2)_d$—$R^7$. In an even more preferred embodiment, $A^8$ is NH or N—$(CH_2)_d$—$R^7$, and $A^9$ is N and $A^{10}$ is CH.

In general formulae 5 and 7, $A^{12}$ and $A^{13}$ are selected from N and C and $A^{14}$, $A^{15}$ and $A^{16}$ are selected from NH, N—$CH_3$, S, N and CH. Again, these atoms constitute an aromatic five-membered ring and so there must be one, and only one, S or trigonal nitrogen. Hence the selection of $A^{12}$, $A^{13}$, $A^{14}$, $A^{15}$ and $A^{16}$ is subject to the following restrictions.
1) One of $A^{14}$, $A^{15}$ and $A^{16}$ is NH, N—$CH_3$ or S or one of $A^{12}$ and $A^{13}$ is N.
2) Not more than one of $A^{14}$, $A^{15}$ and $A^{16}$ is NH, $N\_CH_3$ or S.
3) $A^{12}$ and $A^{13}$ may not both simultaneously be N.
4) If one of $A^{14}$, $A^{15}$ and $A^{16}$ is NH, N—$CH_3$ or S then $A^{12}$ and $A^{13}$ are both C As used herein, the term "alkyl" or "alkyl group" is intended to designate lower alkyl groups, i.e. saturated hydrocarbon groups of between one and six carbon atoms, including linear, branched and cyclic alkyl groups. Examples of "alkyl" include, but are not limited to: $C_1$-methyl, $C_2$-ethyl, $C_3$-propyl, isopropyl, cyclopropyl, $C_4$-n-butyl, sec-butyl, isobutyl, tert-butyl, cyclobutyl, cyclopropylmethyl, methylcyclopropyl, $C_5$-n-pentyl, neopentyl, cyclopropylethyl, dimethylcyclopropyl, and $C_6$-n-hexyl, cyclohexyl, bicyclo[3.1.0] hexyl.

The term "alkenyl" or "alkenyl group" denotes a lower alkenyl group, i.e. a mono-unsaturated hydrocarbon group of between two and six carbon atoms, including linear, branched and cyclic alkenyl groups. Examples of "alkenyl" include, but are not limited to: $C_2$-vinyl, $C_3$-allyl, 1-methylvinyl, 1-propenyl, $C_4$-but-3-enyl, but-2-enyl, methallyl.

The term "alkynyl" or "alkynyl group" denotes a lower alkynyl group, i.e. an unsaturated hydrocarbon group of between two and six carbon atoms which includes a carbon-carbon triple bond, including linear, branched and cyclic alkynyl groups. Examples of "alkynyl" include, but are not limited to: $C_2$-ethynyl, $C_3$-propargyl, 1-propynyl.

The term "hydroxyalkyl" denotes an alkyl group as defined above in which one or more of the hydrogen atoms are replaced by hydroxyl groups (OH). In general, not more than one hydroxyl group will be attached to any particular carbon atom within the hydroxalkyl group, Examples of hydroxyalkyl groups include, but are not limited to: hydroxymethyl ($HOCH_2$), 1-hydroxyethyl ($CH_3CH(O)$), 2-hydroxyethyl ($HOCH_2CH_2$), 1,2-dihydroxyethyl ($HOCH_2CH(OH)$) 4-hydroxy-2-pentyl ($CH_3CH(OH)CH_2CH(CH_3)$), and 4-hydroxycyclohexyl.

The term "acyl" denotes a group R—C(=O), where R is H, a saturated or unsaturated hydrocarbon moiety of up to seven carbon atoms or a pyridyl or thienyl group. Examples of acyl groups include, but are not limited to: formyl, acetyl, pivaloyl, benzoyl and nicotinoyl.

The compounds according to the present invention generally contain a basic nitrogen atom and so are capable of forming addition salts with protic acids such as hydrochloric acid, sulphuric acid, phosphoric acid, acetic acid, trifluoroacetic acid, benzoic acid, maleic acid, citric acid, fumaric acid, methanesulphonic acid and the like. The compounds of the present invention may also contain an acidic group, such as a carboxylic acid group at R7 or R8 These compounds may exist as inner salts (zwitterions) or as salts such as sodium, potassium, magnesium, calcium or tetra-alkylammonium salts. To the extent that such salts are pharmaceutically acceptable, they are included within the scope of the present invention.

The compounds according to the present invention may have one or more stereogenic centres ("asymmetric carbon atoms") and so may exhibit optical isomerism. The scope of the present invention includes all epimers, enantiomers and diastereomers of compounds according to general formula 1, including single isomers, mixtures and racemates.

Particularly preferred embodiments within the present invention are those compounds that combine two or more of the preferred features described above.

One such particularly preferred embodiment is a urea according to general formula 8.

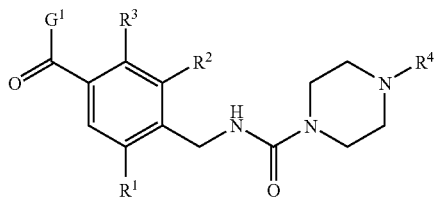

8

In general formula 8, $R^1$, $R^2$, $R^3$, $R^4$ and $G^1$ are as previously defined.

Another particularly preferred embodiment is a compound according to general formula 9, which corresponds to a compound according to general formula 1 in which $G^1$ is a group according to general formula 6 wherein $A^4$, $A^5$ and $A^{10}$ are all CH, $A^6$ is NH, $A^7$ and $A^{11}$ are both C, $A^8$ is $N(CH_2)_dR^7$ and $A^9$ is N.

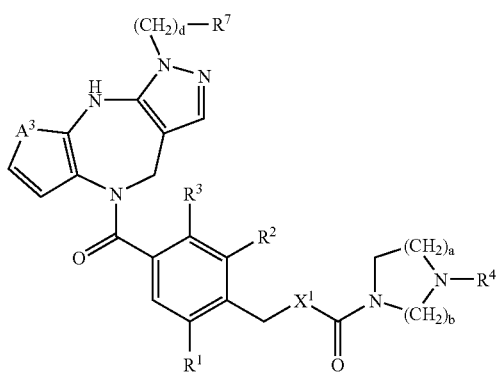

9

In general formula 9, $R^1$, $R^2$, $R^3$, $R^4$, $R^7$, $A^3$, $X^1$, a, b and d are as previously defined.

A most preferred embodiment is a compound according to general formula 10.

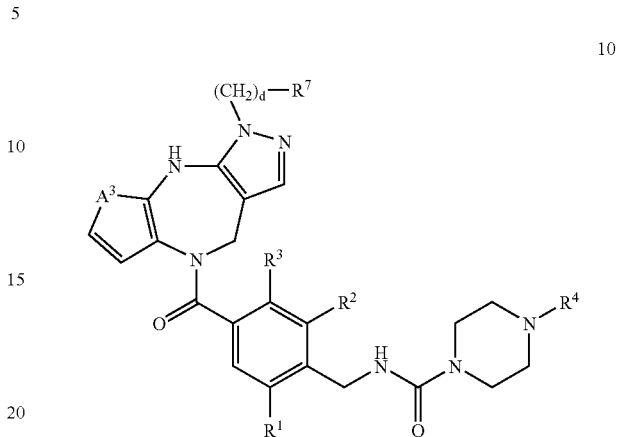

10

In general formula 10, $R^1$, $R^2$, $R^3$, $R^4$, $R^7$, $A^3$ and d are as previously defined.

Individual preferred compounds within the invention include:
4-(3,3-Dimethyl-butyl)-piperazine-1-carboxylic acid 2-methyl-A-(3-methyl-4,10-dihydro-3H-2,3,4,9-tetraaza-benzo[f]azulene-9-carbonyl)-benzylamide;
4-(2-Cyclopropyl-ethyl)-piperazine-1-carboxylic acid 2-methyl-4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 3-methyl-4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 3-fluoro-4-(3-methyl-4,10-dihydro-3H-2,3,4,9-tetraaza-benzo[f]azulene-9-carbonyl)-benzylamide;
4-(2-Hydroxymethyl-cyclopropylmethyl)-piperazine-1-carboxylic acid-2-methyl-4-(3-methyl-4,10-dihydro-3H-2,3,4,9-tetraaza-benzo[f]azulene-9-carbonyl)-benzylamide;
4-(3-Methyl-butyl)-piperazine-1-carboxylic acid 2-methyl-4-(3-methyl-4,10-dihydro-3H-2,3,4,9-tetraaza-benzo[f]azulene-9-carbonyl)-benzylamide;
4-Cyclopentylmethyl-piperazine-1-carboxylic acid 2-methyl-4-(3-methyl-4,10-dihydro-3H-2,3,4,9-tetraaza-benzo[f]azulene-9-carbonyl)-benzylamide;
4-Cyclohexylmethyl-piperazine-1-carboxylic acid 2-methyl-4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 3-chloro-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 3-chloro-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 2-methyl-4-(3-methyl-4,10-dihydro-3H-2,3,4,9-tetraaza-benzo[f]azulene-9-carbonyl)-benzylamide;
4-(2-Cyclopropyl-ethyl)-piperazine-1-carboxylic acid 3-methyl-4-(3-methyl-4,10-dihydro-3H-2,3,4,9-tetraaza-benzo[f]azulene-9-carbonyl)-benzylamide;
4-Pentyl-piperazine-1-carboxylic acid 2-methyl-4-(3-methyl-4,10-dihydro-3H-2,3,4,9-tetraaza-benzo[f]azulene-9-carbonyl)-benzylamide;

4-Hexyl-piperazine-1-carboxylic acid 2-methyl-4-(3-methyl-4,10-dihydro-3H-2,3,4,9-tetraaza-benzo[f]azulene-9-carbonyl)-benzylamide;
(R)-4-(2-Methyl-butyl)-piperazine-1-carboxylic acid 2-methyl-4-(3-methyl-4,10-dihydro-3H-2,3,4,9-tetraaza-benzo[f]azulene-9-carbonyl)-benzylamide;
4-(2-Ethyl-butyl)-piperazine-1-carboxylic acid 2-methyl-4-(3-methyl-4,10-dihydro-3H-2,3,4,9-tetraaza-benzo[f]azulene-9-carbonyl)-benzylamide;
4-(2-Methyl-but-2-enyl)-piperazine-1-carboxylic acid 2-methyl-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid-3-methyl-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 3-fluoro-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 2-fluoro-4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 2-fluoro-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 2-methyl-4-(3-methyl-4,10-dihydro-3H-2,3,4,9-tetraaza-benzo[f]azulene-9-carbonyl)-benzylamide;
4-Cyclobutylmethyl-piperazine-1-carboxylic acid 2-chloro-4-(3-methyl-4,10-dihydro-3H-2,3,4,9-tetraaza-benzo[f]azulene-9-carbonyl)-benzylamide;
4-Cyclopropylmethyl-piperazine-1-carboxylic acid 2-chloro-4-(3-methyl-4,10-dihydro-3H-2,3,4,9-tetraaza-benzo[f]azulene-9-carbonyl)-benzylamide; and
4-Cyclobutylmethyl-piperazine-1-carboxylic acid 3-methoxy-4-(3-methyl-4,10-dihydro-3H-2,3,4,9-tetraaza-benzo[f]azulene-9-carbonyl)-benzylamide.

Other individual preferred compounds, especially for treatment of primary dysmenorrhoea, and also for treatment of pre-term labour, Raynauld's disease, brain oedema, motion sickness, small cell lung cancer, depression, anxiety, hyponatremia, liver cirrhosis or congestive heart failure, within the invention include:
4-Cyclopropylmethyl-piperazine-1-carboxylic acid 2-methyl-4-(3-methyl-4,10-dihydro-3H-2,3,4,9-tetraaza-benzo[f]azulene-9-carbonyl)-benzylamide; and
4-(3-Methylsulfanyl-propyl)-piperazine-1-carboxylic acid 2-methyl-4-(3-methyl-4,10-dihydro-3H-2,3,4,9-tetraaza-benzo[f]azulene-9-carbonyl)-benzylamide.

These individually preferred compounds have several advantages over existing entities. They are selective for the $V_{1a}$ receptor over other AVP receptors. Thus they are potentially safer and more effective than existing non-selective entities. Existing $V_{1a}$ selective entities have been suspended during development due to issues such as safety. Furthermore, they are non-peptidic small molecules. It is well known that such compounds have significantly more potential to be orally active than peptides. As such they offer more convenience and better patient compliance than peptidic entities.

The compounds of the present invention can be prepared by standard chemical manipulations. In general, compounds according to general formula 1 can be considered to consist of three component parts:

Component $C^1$ corresponding to $G^1$
Component $C^2$ corresponding to the substituted benzoyl unit
Component $C^3$ corresponding to the saturated heterocycle

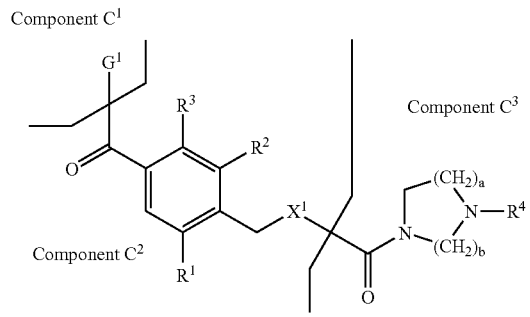

Intermediates corresponding to these components are prepared and then assembled to give the final product, These three components are:
(i) for $C^1$, a secondary amine $G^1$-H
(ii) for $C^2$, a substituted benzoic acid

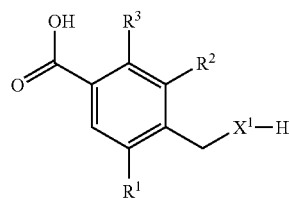

(iii) for $C^3$, a monosubstituted saturated heterocycle

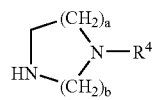

It will be recognised that the substituted benzoic acid that serves for $C^2$ has two functional groups, one of which will need temporary protection during the assembly of the final compound. The principles of functional group protection are well known in the art and are described in, for example, J. F. W. McOmie, "Protective Groups in Organic Chemistry", Plenum Press, 1973; T. W. Greene and P. G. M. Wuts, "Protective Groups in Organic Synthesis", 2$^{nd}$ edition, John Wiley, 1991; and P. J. Kocienski, "Protecting groups", Georg Thieme Verlag, 1994. The carboxylic acid group will usually be protected as an ester, such as the methyl, benzyl or tert-butyl ester. The primary amine of the benzoic acid (when $X^1$=NH) will usually be protected as a carbamate derivative such as the tert-butyl carbamate (BOC derivative), the benzyl carbamate (CBZ or more simply Z derivative) or the 9-fluorenylmethyl carbamate (Fmoc derivative). When $X^1$=O the resulting alcohol function will usually be protected as an ester such as an acetate, or an ether such as a methoxymethyl, tetrahydropyranyl or trialkylsilyl ether. Other functional groups may require protection. For example, the group $G^1$ may include one or more primary or secondary amino groups which may need protection. In the following general description of the synthetic methodology it will be assumed that such protection is used when necessary.

(i) Preparation of Secondary Amine for $C^1$

Acyclic secondary amines corresponding to $HNR^5R^5$ are well known. Many are items of commerce. Those that are not may be prepared according to published methods or by simple modification of such methods. Some particularly useful methods are listed below.

a) Alkylation

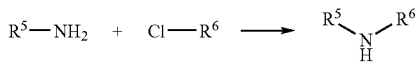

(This method is only applicable in cases where further alkylation can be avoided.)

b) Reductive Amination

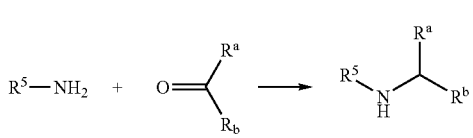

(where $R^aCHR^b$ corresponds to $R^6$)

c) Amide Reduction

(where $R^aCH_2$ corresponds to $R^6$)

The starting amide can itself be prepared using well known methods.

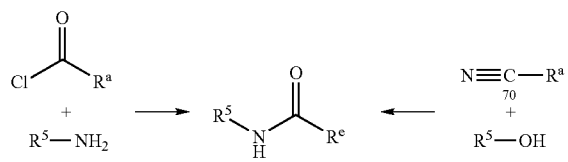

Secondary amines corresponding to $C^1$ where $G^{11}$ is a group according to general formulae 3-7 are generally not commercially available. They can be prepared according to published methods, or by obvious modifications of such methods. Particularly useful methods are described in: Aranapakam et al., Bioorg. Med. Chem. Lett. 1993, 1733; Artico et al., Farmaco. Ed. Sci. 24, 1969, 276; Artico et al., Farmaco. Ed. Sci. 32, 1977, 339; Chakrabarti et al., J. Med. Chem. 23, 1980, 878; Chakrabarti et al., J. Med. Chem. 23, 1980, 884; Chakrabarti et al., J. Med. Chem. 32, 1989, 2573; Chimirri et al., Heterocycles 36, 1993, 601; Grunewald et al., J. Med. Chem. 39, 1996, 3539; Klunder et al., J. Med. Chem. 35, 1992, 1887; Liegéois et al., J. Med. Chem. 37, 1994, 519; Olagbemiro et al., J. Het. Chem. 19, 1982, 1501; Wright et al., J. Med. Chem. 23, 1980, 462; Yamamoto et al., Tet. Lett. 24, 1983, 4711; and International patent application, publication number WO99/06403.

(ii) Preparation of Substituted Benzoic Acid for $C^2$

Substituted benzoic acids corresponding to $C^2$ are not generally items of commerce, but they can be prepared using published methods or obvious variations of such methods.

The main challenge is generally the elaboration of the $—CH_2X^1H$ functionality at the 4-position. Some useful transformations are listed below.

a) Bromination/Substitution

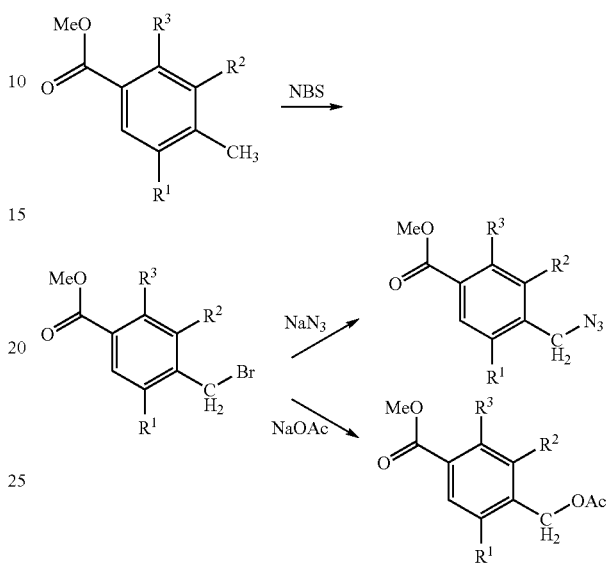

b) Sandmeyer Reaction/Reduction

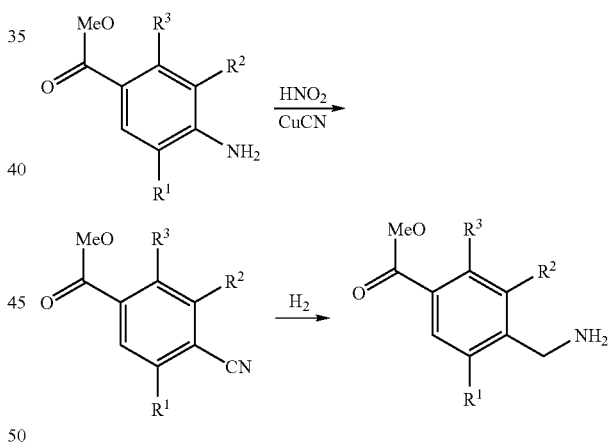

(iii) Preparation of Heterocycle Derivative for $C^3$

Certain heterocycles corresponding to $C^3$, particularly N-aryl piperazines, are items of commerce. Other heterocycles can be prepared according to the methods described in the literature. Useful transformations include the following.

a) Alkylation or Reductive Alkylation

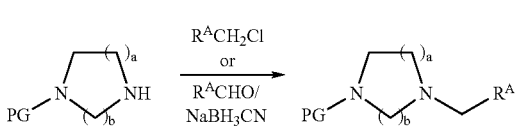

(where PG is a protecting group and $R^4CH_2$ is $R^4$ b) Acylation/Reduction

c) Reduction

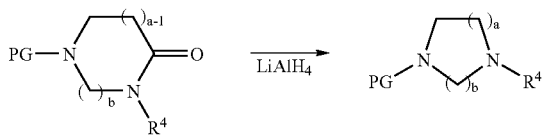

With the three components, suitably protected if necessary, in hand, the assembly of the final compound requires the formation of two bonds: between $C^1$ and $C^2$, and between $C^2$ and $C^3$. These bond-forming steps may be taken in either order. Thus, the following sequences can be proposed:

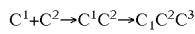

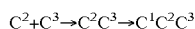

(i) Formation of $C^1$—$C^2$ Bond

The bond between $C^1$ and $C^2$ is a simple amide bond. The chemistry for making such bonds from a carboxylic acid and a secondary amine is well known in the art of organic synthesis, and particularly in the field of peptide synthesis. The carboxylic acid may be converted into a more reactive species such as an acid chloride (using, for example oxalyl chloride or thionyl chloride) or a mixed anhydride (using isobutyl chloroformate). This reactive species is then added to the secondary amine in a suitable solvent, generally an aprotic solvent such as dichloromethane or dimethylformamide, in the presence of a base such as triethylamine or 4-dimethylaminopyridine, and the reaction is allowed to proceed at a temperature between −20° C. and the boiling point of the solvent. The choice of temperature and the time allowed for the reaction will depend on the reactivity of the two components.

Alternatively, the carboxylic acid and the secondary amine may be mixed in a suitable solvent as above, optionally in the presence of a base, and a condensing agent added. Suitable condensing agents include carbodiimides, such as dicyclohexylcarbodiimide (DCC) and N-ethyl-N'-dimethylaminopropylcarbodiimide (EDC, also WSCD for water-soluble carbodiimide), phosphorus reagents such as (benzotriazol-1-yloxy)tris(dimethylamino)phosphonium hexafluorophosphate (BOP), (benzotriazol-1-yloxy)tripyrrolidinophosphonium hexafluorophosphate (PyPBOP®) and bromotripyrrolidinophosphonium hexafluorophosphate (PyBroP®), and ureas such as O-(benzotriazol-1-yl)-N,N,N',N'-tetramethyluronium hexafluorophosphate (HBTUL).

(ii) Formation of $C_2$—$C_3$ Bond

The bond between $C^2$ and $C^3$ is a carbamate (when $X^1$=O) or a urea (when $X^1$=NH). The first step in the formation of this bond is generally to react the heterocycle derivative with phosgene or a phosgene equivalent such as trichloromethyl chloroformate, bis(trichloromethyl)carbonate or carbonyldiimidazole. Again, an aprotic solvent and a tertiary amine base will generally be used. The intermediate formed in this step is usually not isolated. The alcohol ($X^1$=O) or amine ($X^1$=NH) is added and the reaction is allowed to continue, directly forming the carbamate or urea. As an alternative, when $X^1$=NH the reactive intermediate may be formed by the reaction of $C^2$ with the phosgene equivalent and the amine added in the second part of the synthesis.

The compounds according to the present invention are useful in human and animal therapy.

As stated above, the second, third and fourth aspect of the present invention relates to pharmaceutical compositions comprising the above described compounds and to the manufacture of pharmaceutical compositions using the above described compounds. In such pharmaceutical compositions, the above described compounds constitutes a pharmaceutically active ingredient. It may be the sole active ingredient, or it may be combined by at least one other active ingredient or agent. Preferably the pharmaceutical composition includes no additional active agents. Normally, the pharmaceutical compositions according to the invention, used according to the invention or produced according to the invention also comprise other substances, such as an inert vehicle, or pharmaceutical acceptable adjuvants, carriers, preservatives etc., which are well known to persons skilled in the art.

The pharmaceutical composition according to the present invention may be presented in any form that is known in the art. For example, the formulation may be presented as a tablet, capsule, powder, suppository, cream, solution or suspension, or in a more complex form such as an adhesive patch. The formulation will generally include one or more excipients, such as diluents, bulking agents, binding agents, dispersants, solvents, preservatives, flavouring agents and the like. Where the formulation is presented as a tablet or capsule the excipients may optionally include one or more agents to control the release of the active species, such as a coating of a polymer that is insoluble at low pH but soluble at neutral or high pH. Such a coating (known as an "enteric coating") prevents the release of the active agent in the stomach but allows its release in the intestines.

The compounds according to the present invention are useful for treatment of several diseases, disorders or conditions. The term "treatment" used herein relates to both treatment in order to cure or alleviate a disease, disorder or a condition, and to treatment in order to prevent the development of a disease, disorder or a condition. The treatment may either be performed in an acute or in a chronic way. The human or animal to be treated, i.e. the patient, may be any human or non-human mammal in need of treatment according to the invention.

The novel compounds of the present invention are potent and selective OT agonists and/or $V_{1a}$ receptor antagonists and so they and pharmaceutical compositions comprising them are useful in the treatment of treatment of conditions for which inadequate oxytocin-like activity is implicated in the pathophysiology and in the treatment of conditions in which inappropriate vasopressin-like activity is implicated in the pathophysiology. Conditions for which inadequate oxytocin-like activity is implicated in the pathophysiology include, but are not limited to: sexual disorders such as male erectile dysfunction, ejaculatory disorders and female sexual dysfunction, cancer of the prostate, breast, ovary and bones, osteoporosis, benign prostatic hyperplasia, postpartum bleeding, and depression. Conditions in which inappropriate vasopressin-like activity is implicated in the pathophysiology include disorders affecting blood platelets, blood vessels, hepatocytes, brain and uterus-cervix. The novel $V_{1a}$ receptor antagonist and/or pharmaceutical compositions comprising them are suitable for treatment of primary dysmenorrhoea, pre-term labour, hypertension, Raynauld's disease, brain oedema, motion sickness, small cell lung cancer, depression, anxiety, hyponatremia, liver cirrhosis and congestive heart failure. In a preferred embodiment, the compounds or pharmaceutical compositions according to the invention are used for treatment of primary dysmenorrhoea.

Further aspects of the invention relates to methods for treatment of the above mentioned diseases, disorders or conditions, and preferably a method for treatment of primary dysmenorrhoea. According to the method according to the invention a therapeutically effective amount of the compound, or of the pharmaceutical composition, described above is administered to a patient in need of this treatment.

The term "therapeutically effective amount" relates to an amount that will lead to the desired therapeutical effect. The therapeutically effective amount will be determined by the attending physician taking into consideration all appropriate factors. Generally a single dose will comprise between 0.1 mg and 1000 mg, preferably between 1 mg and 250 mg, of the active compound according to the invention. The dose may be given on a single occasion or repeatedly. When given repeatedly, it may be given at regular intervals, such as once, twice or three times daily, or on demand, according to the condition being treated.

When used as therapeutic agents, the compositions of the present invention may be administered by any appropriate route that is known in the art. For example, they may be administered by the oral, buccal, sublingual, rectal, intravaginal, nasal, pulmonary or transdermal routes. Alternatively, they may be given by injection, including intravenous, subcutaneous and intramuscular injection.

For long-term treatment an alternative to repeated dosing may be the administration of a depot dose. For this method of administration the active agent is generally introduced into a matrix of biodegradable polymer, such as a copolymer of lactic and glycolic acids, and the formulation is given either subcutaneous (s.c.) or intramuscularly (i.m.) so as to form a deposit from which the active agent is released as the polymer degrades.

In order to decide whether or not a compound having general formula I is a selective $V_{1a}$ antagonist the compound may be assayed to determine its ability to inhibit the cellular consequences of AVP stimulation on intact cells. In the assay, the compounds cause significant inhibition of cellular activation at concentrations of 30 μM or less. Preferred compounds cause significant inhibition at concentrations of 300 nM or less.

The present invention is further illustrated in the following examples, which are intended to demonstrate the application of the invention but not to limit the scope thereof.

EXAMPLES

The following abbreviations are used:
Bu butyl-alkyl residues may be further denoted as n (normal, i.e. unbranched), i (iso) and t (tertiary)
DIEA N,N-diisopropylethylamine
DMF dimethylformamide
Et ethyl
EtOAc ethyl acetate
HOBt 1-hydrbxybenzotriazole
HPLC high pressure liquid chromatography
h hour(s)
Me methyl
MS mass spectrum
NMR nuclear magnetic resonance spectrum—NMR spectra were recorded in $CDCl_3$ unless otherwise indicated
OVA ornithine vasotocin analogue
pet. petroleum ether boiling in the range 60-80° C.
ether
Ph phenyl
Pn pentyl
Pr propyl
THF tetrahydrofuran
WSCD water-soluble carbodiimide (N-ethyl-N'-(3-dimethylaminopropyl)-carbodiimide hydrochloride Examples 1-13 describe the synthesis of intermediates. Compounds according to the present invention are described in Examples 14-149. Example 150 describes how compounds can be assayed based on their ability to inhibit the cellular consequences of AVP stimulation on intact cells. Example 151 describes tablets for oral administration comprising a compound according to the invention.

Example 1

1-Benzyl-4,10-dihydropyrazolo[5,4-b][1,5]benzodiazepine

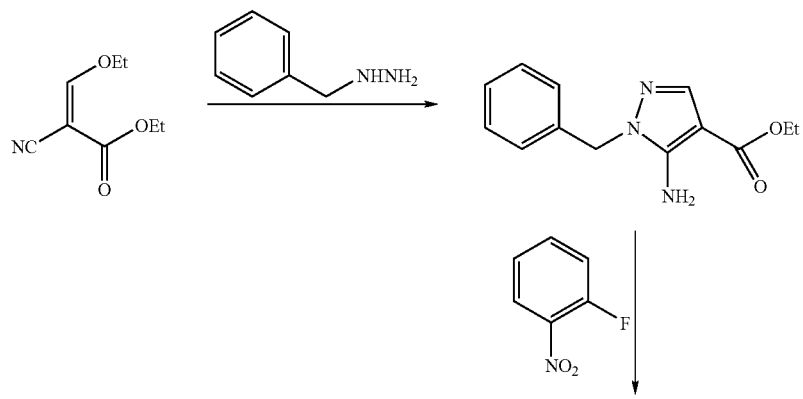

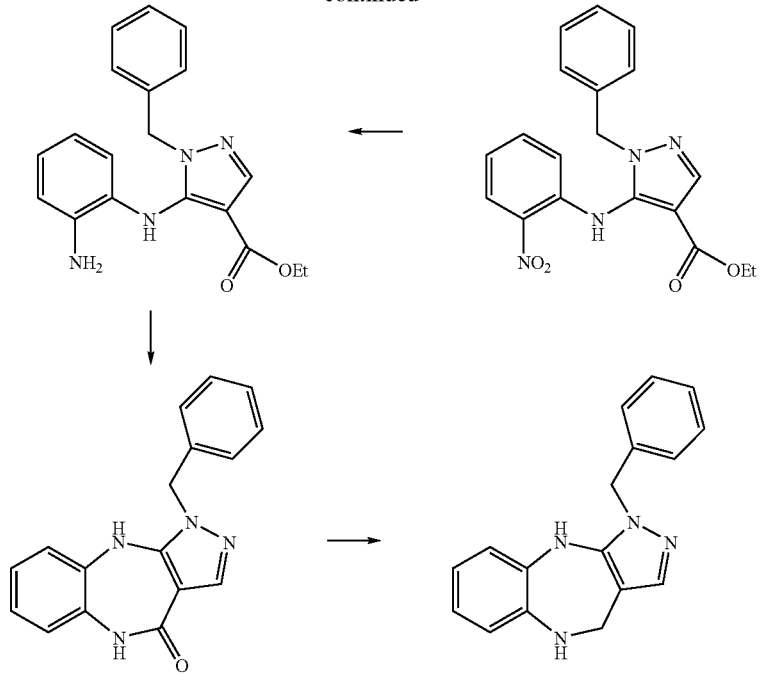

1A: Ethyl 5-amino-1-benzylpyrazole-4-carboxylate

Benzylhydrazine dihydrochloride (4.29 g, 22 mmol) was added to a solution of ethyl (ethoxymethylene)cyanoacetate (3.38 g, 20 mmol) and triethylamine (6.15 ml, 44 mmol, 2 eq) in ethanol (40 ml) and the mixture was heated at reflux for 18 h. The solvent was removed in vacuo and the residue was purified by flash chromatography on silica gel (eluant 60% pet. ether/40% ethyl acetate) to yield a pale yellow solid identified as ethyl 5-amino-1-benzylpyrazole-4-carboxylate (4.3 g, 88%).

1B: Ethyl 1-benzyl-5-(2'-nitrophenylamino)pyrazole-4-carboxylate

Sodium hydride (60% dispersion in oil, 520 mg, 13 mmol) was added portionwise to a suspension of ethyl 5-amino-1-benzylpyrazole-4-carboxylate (2.2 g, 9 mmol) in anhydrous THF (30 ml) at 0° C. The mixture was allowed to warm to room temperature and stirred for 2 h then 1-fluoro-2-nitrobenzene (1.26 g, 9 mmol) was added and the resultant deep purple suspension was stirred at room temperature for 18 h. 1 M KHSO$_4$ was added to quench the reaction and the solvent was removed in vacuo. The residue was dissolved in ethyl acetate and the solution was washed with 0.3 M KHSO$_4$, sat. NaHCO$_3$ and brine, dried over Na$_2$SO$_4$ and concentrated in vacuo. The residue was purified by flash chromatography on silica gel (eluant 75% pet. ether/25% ethyl acetate) to yield ethyl 1-benzyl-5-(2'-nitrophenylamino)pyrazole-4-carboxylate (2.5 g, 76%).

MS [M+H]$^+$ 366.8

1C: Ethyl 5-(2'-aminophenylamino)-1-benzylpyrazole-4-carboxylate

Ethyl 1-benzyl-5-(2'-nitrophenylamino)pyrazole-4-carboxylate (2.5 g, 6.8 mmol) was dissolved in ethyl acetate/ethanol (1:1, 100 ml) and hydrogenated over 10% Pd/C catalyst for 70 minutes. The mixture was filtered through Celite® filter agent and the filtrate was concentrated in vacuo to give a white solid identified as ethyl 5-(2'-aminophenylamino)-1-benzylpyrazole-4-carboxylate (1.5 g, 86%).

MS [M+H]$^+$ 337.2

1D: 1-Benzyl-4,10-dihydropyrazolo[5,4-b][1,5]benzodiazepin-4(5H)-one

A solution of ethyl 5-(2'-aminophenylamino)-1-benzylpyrazole-4-carboxylate (1.75 g, 5.2 mmol) in acetic acid/2-propanol (1:9, 40 ml) was heated at reflux for 3 days. The solvent was removed in vacuo and the residue was azeotroped with toluene to give an off-white solid that was purified by flash chromatography on silica gel (eluant 35% pet. ether/65% ethyl acetate) to yield a white solid identified as 1-benzyl-4,10-dihydropyrazolo[5,4-b][1,5]benzodiazepin-4(5H)-one (780 mg, 52%).

MS [M+H]$^+$ 291.1

1E: 1-Benzyl-4,10-dihydropyrazolo[5,4-b][1,5]benzodiazepine

LiAlH$_4$ (365 mg, 10 mmol) was added portionwise to a suspension of 1-benzyl-4,10-dihydropyrazolo[5,4-b][1,5]benzodiazepin-4(5H)-one (780 mg, 2.7 mmol) in anhydrous THF (15 ml) at 0° C. over 10 min. The resulting suspension was heated at reflux for 18 h, then allowed to cool to room temperature. A further portion of LiAlH$_4$ (90 mg, 2.5 mmol) was added and the mixture was heated at refluxed for 3 h. The mixture was cooled to 0° C., 35% ammonia solution (1 ml) was added dropwise over 10 min and the mixture was stirred at room temperature for 1 h. The resulting suspension was filtered through Celite® filter agent and the filtrate was concentrated in vacuo to give a white solid identified as 1-benzyl-4,10-dihydropyrazolo[5,4-b][1,5]benzodiazepine (450 mg, 60%).

MS [M+H]$^+$ 276.9

Example 2

1-Methyl-4,10-dihydropyrazolo[4,5-c]pyrido[2,3-b][1,4]diazepine

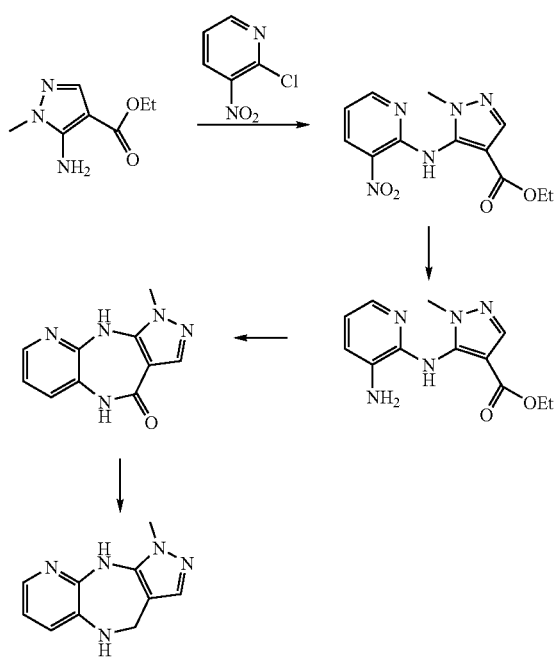

2A: Ethyl 1-methyl-2-3'-nitro-2'-pyridylamino)pyrazole-4-carboxylate

Sodium hydride (60% dispersion in oil, 600 mg, 15 mmol) was added portionwise to a suspension of ethyl 5-amino-1-methylpyrazole-4-carboxylate (1.69 g, 10 mmol) in anhydrous THF (15 ml) at 0° C. The mixture was stirred for 2 h at room temperature then 2-chloro-3-nitropyridine (1.58 g, 10 mmol) was added and the resulting deep red suspension was stirred at room temperature for 18 h. 1 M KHSO$_4$ was added to quench the reaction and the solvent was removed in vacuo. The residue was dissolved in ethyl acetate and the solution was washed with 0.3 M KHSO$_4$, sat NaHCO$_3$ and brine, dried over Na$_2$SO$_4$ and concentrated in vacuo. The residue was purified by flash chromatography on silica gel (eluant 30% pet. ether/70% ethyl acetate) to give ethyl 1-methyl-2-(3'-nitro-2'-pyridylamino)pyrazole-4-carboxylate (1.95 g, 67%).

MS [M+H]$^+$ 292.0

2B: Ethyl 2-(3'-amino-2'-pyridylamino)-1-methylpyrazole-4-carboxylate

A solution of ethyl 1-methyl-2-(3'-nitro-2'-pyridylamino)pyrazole-4-carboxylate (1.95 g, 6.7 mmol) in ethanol (100 ml) was hydrogenated over 10% Pd/C catalyst for 3 h. The reaction mixture was filtered through Celite® filter agent and the filtrate was concentrated in vacuo to give a white solid identified as ethyl 2-(3'-amino-2'-pyridylamino)-1-methylpyrazole-4-carboxylate (1.5 g, 86%).

2C: 1-Methyl-4,10-dihydropyrazolo[4,5-c]pyrido[2,3-b][1,4]diazepin-4(5H)-one

A solution of ethyl 2-(3'-amino-2'-pyridylamino)-1-methylpyrazole-4-carboxylate (1.5 g, 5.75 mmol) in acetic acid/2-propanol (1:9, 50 ml) was heated at reflux for 3 days. The solvent was removed in vacuo and the residue was azeotroped with toluene. The residue was purified by recrystallization from ethanol and then flash chromatography on silica gel (eluant 95% chloroform/4% methanol/1% acetic acid) to give a white solid identified as 1-methyl-4,10-dihydropyrazolo[4,5-c]pyrido[2,3-b][1,4]diazepin-4(5H)-one (560 mg, 45%).

2D: 1-Methyl-4,10-dihydropyrazolo[4,5-c]pyrido[2,3-b][1,4]diazepine

LiAlH$_4$ (365 mg, 10 mmol) was added portionwise to a suspension of 1-methyl-4,10-dihydropyrazolo[4,5-c]pyrido[2,3-b][1,4]diazepin-4(5H)-one (560 mg, 2.6 mmol) in anhydrous THF (30 ml) at 0° C. over 10 minutes. The resulting suspension was heated at reflux for 18 h. The reaction was cooled to 0° C. and 35% ammonia solution (1 ml) was added dropwise over 10 minutes, then the mixture was stirred at room temperature for 1 h. The resulting suspension was filtered through Celite® filter agent and the filtrate was concentrated in vacuo to give a white solid identified as 1-methyl-4,10-dihydropyrazolo[4,5-c]pyrido[2,3-b][1,4]diazepine (410 mg, 78%).

MS [M+H]$^+$ 202.1.

Example 3 tert-Butyl 4-aminomethyl-3-chlorobenzoate

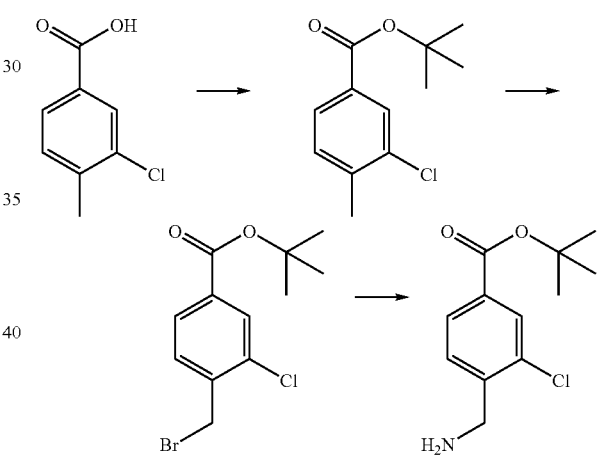

3A: tert-Butyl 3-chloro-4-methylbenzoate

Thionyl chloride (11 ml, 150 mmol) was added to a suspension of 3-chloro-4-methylbenzoic acid (5.12 g, 30 mmol) in toluene (25 ml) and the mixture was heated at reflux for 2 h. The solvent was removed in vacuo and the residue was azeotroped with toluene three times, then dissolved in anhydrous THF (40 ml) and cooled to 0° C. Lithium tert-butoxide (2.4 g, 30 mmol) was added and the mixture was stirred at room temperature for 3 days. Water (5 ml) was added and the solvent was removed in vacuo. The residue was dissolved in ethyl acetate. The solution was washed with 0.3M KHSO$_4$, sat. NaHCO$_3$ and brine, dried over Na$_2$SO$_4$ and concentrated in vacuo to give a pale yellow gum identified as tert-butyl 3-chloro-4-methylbenzoate (5.4 g, 79%).

3B: tert-Butyl 4-bromomethyl-3-chlorobenzoate

N-Bromosuccinimide (4.27 g, 24 mmol) and 2,2'-azo-bis(2-methylpropionitrile) (394 mg, 2.4 mmol) were added to a solution of tert-butyl 3-chloro-4-methylbenzoate (5.4 g, 23.8 mmol) in carbon tetrachloride (75 ml) and the mixture was heated at reflux for 18 h. The solvent was removed in vacuo and the residue was purified by flash chromatography on silica gel (eluant 95% pet.ether/5% ethyl acetate) to give a white solid identified as tert-butyl 4-bromomethyl-3-chlorobenzoate (5.7 g, 78%).

3C: tert-Butyl 4-aminomethyl-3-chlorobenzoate

Ethanol (100 ml) was saturated with ammonia, then tert-butyl 4-bromomethyl-3-chlorobenzoate (5.7 g, 18.7 mmol) was added and the mixture was stirred at room temperature for 2 h. The solvent was removed in vacuo and the residue was triturated with diethyl ether to give a white solid identified as tert-butyl 4-aminomethyl-3-chlorobenzoate (4.1 g, 91%).

Example 4

4-(tert-Butyloxycarbonylaminomethyl)-3-chlorobenzoic acid

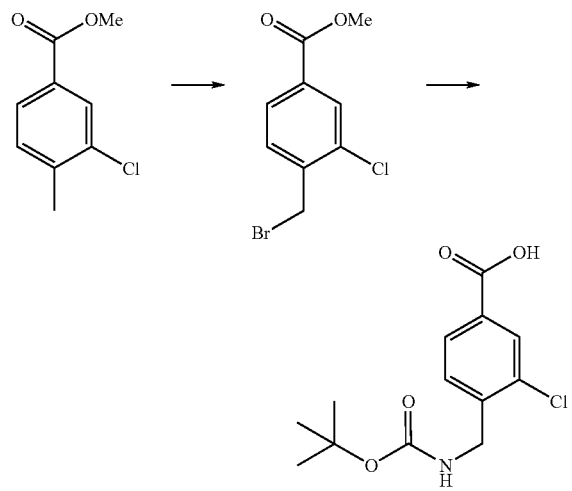

4A. Methyl 4-bromomethyl-3-chlorobenzoate

To a solution of methyl 3-chloro-4-methylbenzoate (5.0 g, 27.1 mmol) in carbon tetrachloride (50 ml) were added N-bromosuccinimide (5.8 g, 32.0 mmol) and 2,2'-azo-bis(2-methylpropionitrile) (0.442 g, 2.70 mmol). The mixture was heated at reflux for 18 h, then allowed to cool to room temperature and concentrated in vacuo. The residue was purified by flash chromatography on silica (eluant pet. ether→5% ethyl acetate/95% pet. ether) to give an oil identified as methyl 4-bromomethyl-3-chlorobenzoate (5.96 g, 84%).

4B. 4-(tert-Butyloxycarbonylaminomethyl)-3-chlorobenzoic acid

To a saturated solution of ammonia in ethanol (170 ml) was added methyl 4 bromomethyl-3-chlorobenzoate from Example 4A (5.5 g, 20.9 mmol). The mixture was stirred at room temperature for 1 h and then concentrated in vacuo. The residue was triturated with diethyl ether and the resultant white crystals were filtered off and washed with more diethyl ether. To a solution of this solid in water (100 ml) were added solutions of di-tert-butyl dicarbonate (5.0 g, 23.0 mmol) in dioxan (100 ml) and sodium hydroxide (1.86 g, 46.0 mmol) in water (100 ml). The mixture was stirred at room temperature for 18 h and then concentrated in vacuo. The aqueous residue was acidified with citric acid and extracted with chloroform/2-propanol. The organic layer was washed with water, dried over MgSO$_4$, and concentrated in vacuo to give a white solid identified as 4-(tert-butyloxycarbonylaminomethyl)-3-chlorobenzoic acid (2.8 g, 67%).

Example 5

4-(tert-Butyloxycarbonylaminomethyl)-3-nitrobenzoic acid

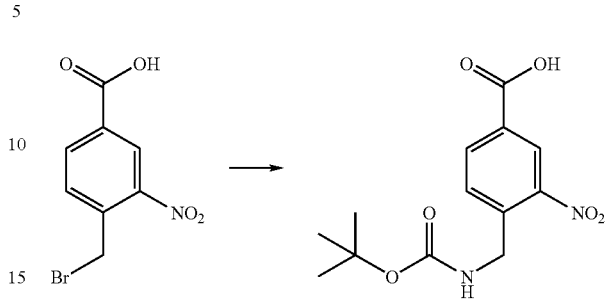

4-Bromomethyl-3-nitrobenzoic acid (4.75 g, 18.2 mmol) was reacted following the method of Example 4B to give a yellow solid identified as 4-(tert-butyloxycarbonylaminomethyl)-3-nitrobenzoic acid (2.6 g, 49%).

Example 6

4-Cyano-3-methylbenzoic acid

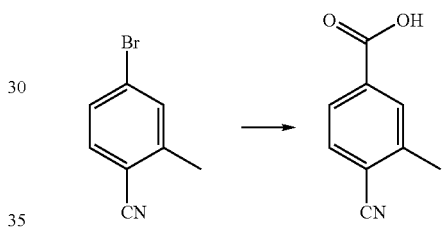

To a solution of 4-bromo-2-methylbenzonitrile (2.0 g, 10.2 mmol) in THF (100 ml) at −78° C. under a nitrogen atmosphere was added dropwise a 2.5 M solution of n-butyl lithium (4.48 ml, 11.2 mmol). The mixture was stirred at −78° C. for 1 h and then poured onto solid carbon dioxide (5 g) in THE (50 ml). The mixture was allowed to warm to room temperature. Water was added (200 ml) and the mixture was extracted with diethyl ether (3 times). The aqueous layer was acidified by addition of concentrated HCl and extracted with chloroform (3 times). The combined chloroform extracts were washed with water, dried over MgSO$_4$, and concentrated in vacuo to give a white solid identified as 4-cyano-3-methylbenzoic acid (1.2 g, 73%).

Example 7

4-Cyano-2-methylbenzoic acid

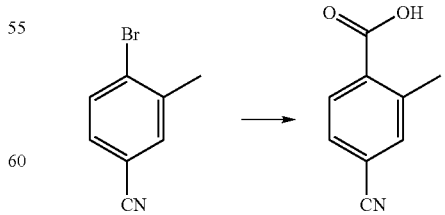

4-Bromo-3-methylbenzonitrile (2.0 g, 10.2 mmol) was reacted following the method of Example 6. The product was triturated with hexane to give a yellow solid identified as 4-cyano-2-methylbenzoic acid (0.96 g, 59%).

Example 8

4-(tert-Butyloxycarbonylaminomethyl)-2-fluorobenzoic acid

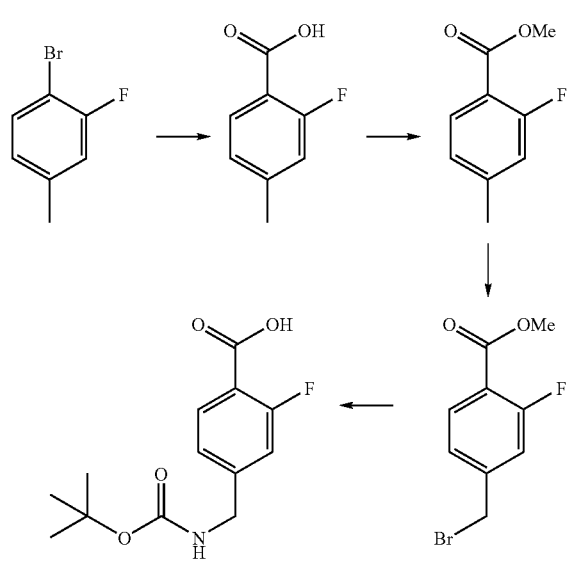

8A. 2-Fluoro-4-methylbenzoic acid

4-Bromo-3-fluorotoluene (8.33 g, 44.07 mmol) was reacted following the method of Example 6 to give a white solid identified as 2-fluoro-4-methylbenzoic acid (4.89 g, 72%).

8B. Methyl 2-fluoro-4-methylbenzoate

To a solution of 2-fluoro-4-methylbenzoic acid (6.04 g, 39.18 mmol) in toluene (80 ml) was added thionyl chloride (65 ml, 89.11 mmol). The mixture was heated at reflux for 2.5 h, cooled and concentrated in vacuo. The residue was dissolved in dichloromethane (50 ml) and methanol (50 ml) was added. The mixture was stirred at room temperature for 2.5 h and then concentrated in vacuo. The residue was dissolved in dichloromethane (100 ml), washed with saturated sodium bicarbonate solution and brine, dried over MgSO$_4$, and concentrated in vacuo to give a tan solid identified as methyl 2-fluoro-4-methylbenzoate (5.07 g, 77%).

8C. Methyl 4-bromomethyl-2-fluorobenzoate

Methyl 2-fluoro-4-methylbenzoate (5.07 g, 30.16 mmol) was reacted following the method of Example of 4A. The product was purified by flash chromatography on silica (eluant 20% ethyl acetate/80% pet. ether) to give an oil identified as methyl 4-bromomethyl-2-fluorobenzoate (5.9 g, 80%).

8D. 4-(tert-Butyloxycarbonylaminomethyl)-2-fluorobenzoic acid

Methyl 4-bromomethyl-2-fluorobenzoate (5.9 g, 24.13 mmol) was reacted following the method of Example 4B. The product was recrystallised from dioxan/pet. ether to give white crystals identified as 4-(tert-butyloxycarbonylaminomethyl)-2-fluorobenzoic acid (2.4 6 g, 38%).

Example 9

4-Cyano-3,5-dimethylbenzoic acid

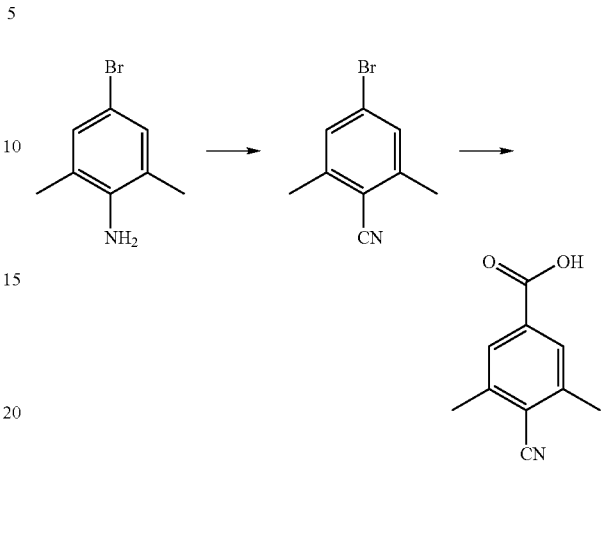

9A. 4-Bromo-2,6-dimethylbenzonitrile

4-Bromo-2,6-dimethylaniline (4.49 g, 22.4 mmol) was taken up in water (25 ml) and concentrated hydrochloric acid (8.0 ml) was added. The mixture was sonicated to form a fine suspension and then cooled to 0° C. A solution of sodium nitrite (1.67 g, 24.2 mmol) in water (5 ml) was then added dropwise so as to maintain the temperature of the reaction between 0-5° C. The mixture was stirred at 0-5° C. for 30 minutes and then neutralised by addition of solid sodium bicarbonate. The resulting solution was then added portionwise to a solution of copper cyanide (2.42 g, 27.0 mmol) and potassium cyanide (3.65 g, 56.1 mmol) in water (25 ml) at 70° C. The mixture was stirred at 70° C. for 30 minutes, allowed to cool and then extracted with toluene (2 times). The combined extracts were washed with water and brine, dried over MgSO$_4$, and concentrated in vacuo. The residue was purified by flash chromatography on silica (eluant 5% ethyl acetate/95% pet. ether) to give an orange solid identified as 4-bromo-2,6-dimethylbenzonitrile (3.2 g, 68%).

9B. 4-Cyano-3,5-dimethylbenzoic acid

4-Bromo-2,6-dimethylbenzonitrile (3.20 g, 15.2 mmol) was reacted following the method of Example 6 to give a tan solid identified as 4-cyano-3,5-dimethylbenzoic acid (1.5 g, 56%).

Example 10

2-Chloro-4-cyanobenzoic acid

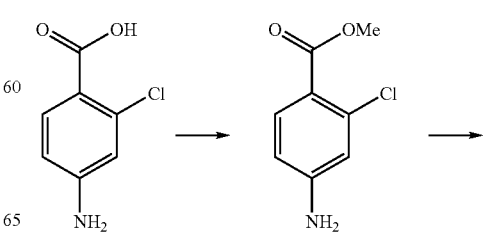

10A. 4-Amino-2-chloro-benzoic acid methyl ester

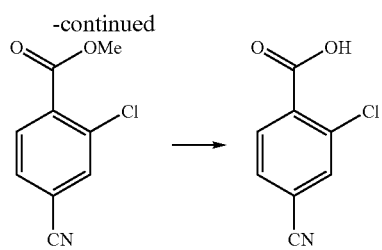

Acetyl chloride (2.5 ml) was added drop-wise to a solution of 2-chloro-4-cyano-benzoic acid (2.22 g, 12.94 mmol) in methanol (75 ml) while stirring. The mixture was heated at reflux for 18 h, cooled and concentrated in vacuo. The residue was taken up in ethyl acetate, washed with saturated NaHCO$_3$ and brine and concentrated in vacuo to give a beige solid identified as 4-amino-2-chloro-benzoic acid methyl ester (2.32 g, 97%).

10B. 2-Chloro-4-cyano-benzoic acid methyl ester

4-Amino-2-chloro-benzoic acid methyl ester (5.00 g, 26.94 mmol) was reacted following the method of Example 9A to give a pale orange solid identified as 2-chloro-4-cyano-benzoic acid methyl ester (2.62 g, 50%).

10C. 2-Chloro-4-cyanobenzoic acid

Lithium hydroxide (1.12 g, 26.69 mmol) was added to a solution of 2-chloro-4-cyano-benzoic acid methyl ester (2.60 g, 13.29 mmol) in dioxan/water (4:1, 100 ml). The mixture was stirred at room temperature for 3 h and concentrated in vacuo. The residue was partitioned between 1N hydrochloric acid and chloroform and the organic layer was washed with brine and concentrated in vacuo. The residue was recrystallised from a mixture of dioxan and pet. ether to give a pale orange solid identified as 2-chloro-4-cyanobenzoic acid (2.33 g, 97%).

Example 11

4-(tert-Butoxycarbonylamino-methyl)-3-fluorobenzoic acid

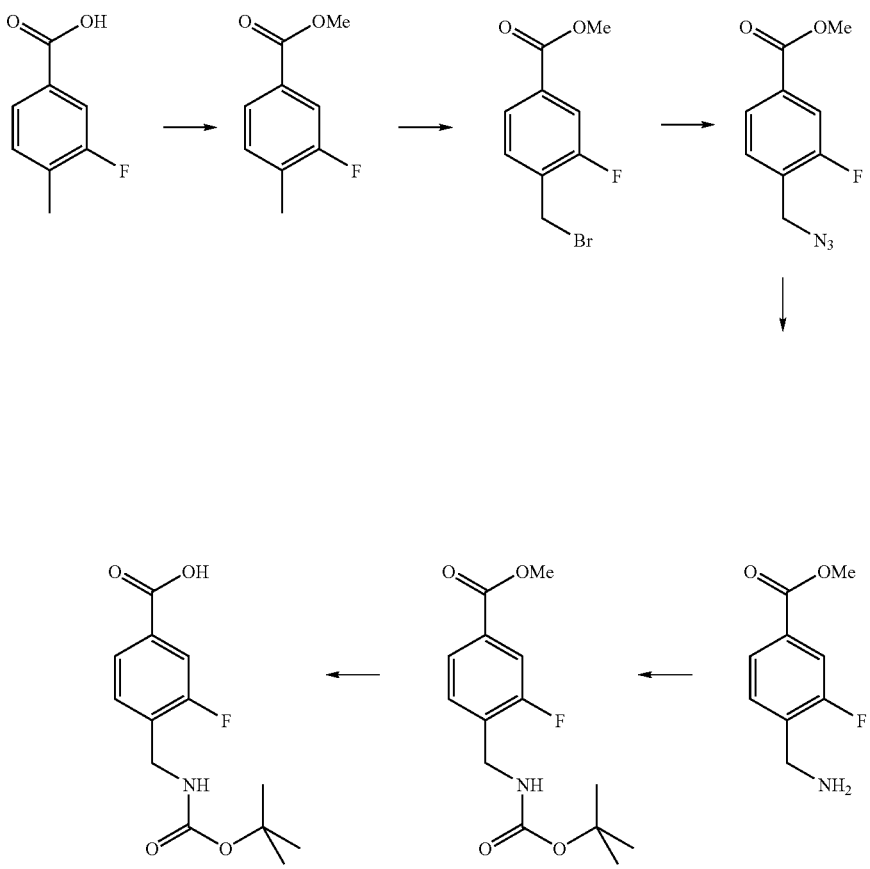

11A. 3-Fluoro-4-methylbenzoic acid methyl ester

3-Fluoro-4-methylbenzoic acid (5.0 g, 32.4 mmol) was reacted following the method of Example 8B to give a brown oil identified as 3-fluoro-4-methylbenzoic acid methyl ester (4.5 g, 83%).

11B. 4-Bromomethyl-3-fluorobenzoic acid methyl ester

3-Fluoro-4-methylbenzoic acid methyl ester (4.5 g, 26.6 mol) was reacted following the method of Example 4A to give a yellow oil identified as 4-bromomethyl-3-fluorobenzoic acid methyl ester (2.7 g, 41%).

11C. 4-Azidomethyl-3-fluorobenzoic acid methyl ester

Sodium azide (609 mg) was added to a solution of 4-bromomethyl-3-fluorobenzoic acid methyl ester (2.1 g, 8.5 mmol) in DMF (30 ml). The mixture was stirred for 18 h, diluted with ethyl acetate, washed with water and brine and concentrated in vacuo to give a colourless oil identified as 4-azidomethyl-3-fluorobenzoic acid methyl ester (1.78 g, 100%).

11D. 4-Aminomethyl-3-fluorobenzoic acid methyl ester

Hydrogen was passed through a degassed solution of 4-azidomethyl-3-fluorobenzoic acid methyl ester (2.11 g, 10 mmol) in methanol containing 10% palladium on carbon for 2 h. The reaction mixture was filtered through Celite® and the filtrate was concentrated in vacuo to give a colourless oil identified as 4-aminomethyl-3-fluorobenzoic acid methyl ester (1.51 g, 83%).

11E. 4-(tert-Butoxycarbonylamino-methyl)-3-fluorobenzoic acid methyl ester

To a solution of 4-aminomethyl-3-fluorobenzoic acid methyl ester (1.5 g, 8.2 mmol) in dichloromethane (20 ml) were added di-tert-butyl dicarbonate (2.3 g, 11 mmol) and triethylamine (1.4 ml, 10 mmol). The mixture was stirred for 18 h, washed with 0.3M KHSO$_4$ and brine and concentrated in vacuo. The residue was purified by flash chromatography on silica gel (eluant 10% EtOAc/pet. ether) to give a white solid identified as 4-(tert-butoxycarbonylamino-methyl)-3-fluorobenzoic acid methyl ester (1.4 g, 60%),

11F. 4-(tert-Butoxycarbonylamino-methyl)-3-fluorobenzoic acid

To a solution of 4-(tert-Butoxycarbonylamino-methyl)-3-fluorobenzoic acid methyl ester (640 mg, 2.25 mmol) in dioxan (40 ml) was added 1N NaOH (4.5 ml, 4.5 mmol). The mixture was stirred for 18 h, diluted with ethyl acetate, washed with 1N KHSO$_4$, water and brine and concentrated in vacuo to give a white solid identified as 4-(tert-butoxycarbonylamino-methyl)-3-fluorobenzoic acid (608 mg, 100%).

Example 12

4-Cyano-3-ethylbenzoic acid

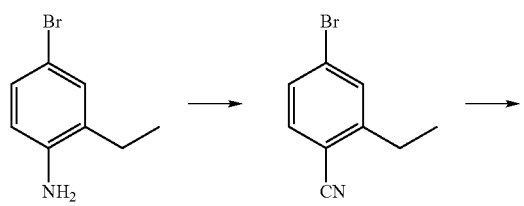

-continued

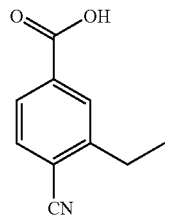

12A. 4-Bromo-2-ethylbenzonitrile

4-Bromo-2-ethylaniline (12.5 g, 62.5 mmol) was reacted following the method of Example 9A to give a pale brown oil identified as 4-bromo-2-ethylbenzonitrile (7.66 g, 58%).

12B. 4-Cyano-3-ethylbenzoic acid

4-Bromo-2-ethylbenzonitrile (7.55 g, 35.9 mmol) was reacted following the method of Example 6 to give a pale brown solid identified as 4-cyano-3-ethylbenzoic acid (4.34 g, 69%).

Example 13

4-Cyano-2-methoxybenzoic acid

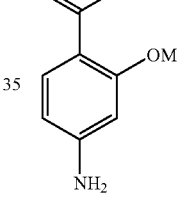 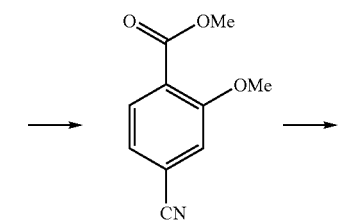

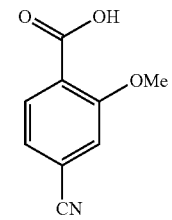

13A. 4-Cyano-2-methoxybenzoic acid methyl ester

4-Amino-2-methoxybenzoic acid methyl ester (4.59 g, 25.33 mmol) was reacted following the method of Example 9A to give a pale yellow solid identified as 4-cyano-2-methoxybenzoic acid methyl ester (2.58 g, 53%).

13B. 4-Cyano-2-methoxybenzoic acid

4-Cyano-2-methoxybenzoic acid methyl ester (2.68 g, 15.52 mmol) was reacted following the method of Example 10C to give a white powder identified as 4-cyano-2-methoxybenzoic acid (2.60 g, 95%).

Example 14

4-(3-Methyl-4-(piperazine-1-carbonylaminomethyl)benzoyl)-5,6,7,8-tetrahydrothieno[3,2-b]azepine hydrochloride

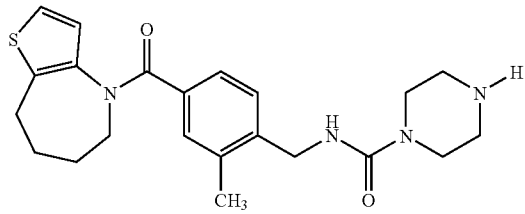

14A: 4-(3-Methyl-4-cyanobenzoyl)-5,6,7,8-tetrahydrothieno[3,2-b]azepine

Thionyl chloride (5 ml, 68.55 mmol) was added to a stirred suspension of 4-cyano-3-methylbenzoic acid (1.43 g, 8.90 mmol) in dichloromethane (20 ml). The mixture was heated at reflux for 2 h, cooled to room temperature and concentrated in vacuo. The residue was azeotroped with dichloromethane then dissolved in dichloromethane 20 ml. The resulting solution was slowly added to a stirred solution of 5,6,7,8-tetrahydrothieno[3,2-b]azepine (1.36 g, 8.90 mmol) and triethylamine (3.70 ml, 26.54 mmol) in dichloromethane (30 ml). The mixture was stirred at room temperature for 24 h, washed with 1M KHSO$_4$, saturated NaHCO$_3$ and brine, then concentrated in vacuo. The residue was purified by flash chromatography on silica gel (eluant 25% EtOAc/pet. ether) to give a brown solid identified as 4-(3-methyl-4-cyanobenzoyl)-5,6,7,8-tetrahydrothieno[3,2-b]azepine (1.70 g, 71%).

14B: 4-(4-Aminomethyl-3-methylbenzoyl)-5,6,7,8-tetrahydrothieno[3,2-b]azepine

Cobalt(II) chloride hexahydrate (2.84 g, 11.94 mmol) was added to a solution of 4-(3-methyl-4-cyanobenzoyl)-5,6,7,8-tetrahydrothieno[3,2-b]azepine (1.70 g, 5.70 mmol) in methanol (70 ml) at 0° C. Sodium borohydride (2.22 g, 58.68 mmol) was added portion wise at 0° C. and the mixture was stirred at 0° C. for 30 min then at room temperature for 2 h. Saturated ammonium chloride was then added and the mixture was stirred for 30 min then concentrated in vacuo. The residue was azeotroped with toluene then extracted with chloroform. The extracts were washed with brine and concentrated in vacuo to give a white solid identified as 4-(4-aminomethyl-3-methylbenzoyl)-5,6,7,8-tetrahydrothieno[3,2-b]azepine (1.12 g, 65%).

14C: 4-(4-(4-(tert-Butyloxycarbonyl)piperazine-1-carbonylaminomethyl)-3-methylbenzoyl)-5,6,7,8-tetrahydrothieno[3,2-b]azepine

1,1'-Carbonyldiimidazole (234 mg, 1.45 mmol) was added to a solution of 4-(4-aminomethyl-3-methylbenzoyl)-5,6,7,8-tetrahydrothieno[3,2-b]azepine (400 mg, 1.33 mmol) and DIEA (0.3 ml, 1.72 mmol) in DMF (20 ml) and the mixture was stirred at room temperature for 30 min. tert-Butyl piperazine-1-carboxylate (281 mg, 1.50 mmol) was added and the mixture was stirred at room temperature for 24 h then concentrated in vacuo. The residue was taken up in chloroform and the solution was washed with 1M KHSO$_4$ and brine, then concentrated in vacuo. The residue was purified by flash chromatography on silica gel (eluant 75% EtOAc/pet. ether) to give a white solid identified as 4-(4-(4-(tert-butyloxycarbonyl)piperazine-1-carbonylaminomethyl)-3-methylbenzoyl)-5,6,7,8-tetrahydrothieno[3,2-b]azepine (588 mg, 86%).

14D: 4-(3-Methyl-4-(piperazine-1-carbonylaminomethyl)benzoyl)-5,6,7,8-tetrahydrothieno[3,2-b]azepine hydrochloride

A solution of 4-(4-(4-(tert-butyloxycarbonyl)piperazine-1-carbonylaminomethyl)-3-methylbenzoyl)-5,6,7,8-tetrahydrothieno[3,2-b]azepine (588 mg, 1.15 mmol) in 4N HCl/dioxan (100 ml) was stirred at room temperature for 30 min then concentrated in vacuo. The residue was dissolved in acetonitrile/water and lyophilised to give a white solid identified as 4-(3-methyl-4-(piperazine-1-carbonylaminomethyl)benzoyl)-5,6,7,8-tetrahydrothieno[3,2-b]azepine hydrochloride (393 mg, 76%).

$^1$H NMR: d$_6$-DMSO δ 1.60-1.74 (2H, m), 1.82-1.94 (2H, m), 2.17 (3H, s), 2.86-2.95 (2H, m), 2.96-3.10 (4H, m), 3.35-3.45 (2H, m), 3.50-3.64 (4H, m), 4.16 (2H, s), 6.26 (1H, br s); 6.85-7.10 (4H, m), 7.24 (1H, br s), 9.28 (1H, br s) ppm. MS: [M+H]$^+$=413.2

Example 15

5-(4-(4-Cyclopropylmethylpiperazine-1-carbonylaminomethyl)-3-methylbenzoyl)-1-methyl-4,10-dihydropyrazolo[5,4-b][1,5]benzodiazepine

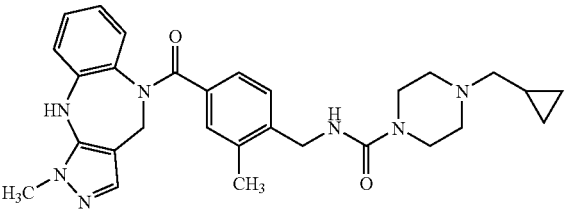

15A: 5-(4-Cyano-3-methylbenzoyl)-1-methyl-4,10-dihydropyrazolo[5,4-b]-[1,5]benzodiazepine

Thionyl chloride (1.8 ml, 27 mmol) was added to a stirred suspension of 4-cyano-3-methylbenzoic acid (1.29 g, 8.0 mmol) in toluene (25 ml). The mixture was heated at reflux for 2 h, cooled to room temperature and concentrated in vacuo. The residue was azeotroped with toluene then dissolved in dichloromethane (10 ml). The resulting solution was added to a stirred suspension of 1-methyl-4,10-dihydropyrazolo[5,4-b][1,5]benzodiazepine (1.6 g, 8 mmol) and triethylamine (1.4 ml, 10 mmol) in dichloromethane (15 ml). The mixture was stirred overnight at room temperature then concentrated in vacuo. The residue was partitioned between chloroform and 0.3M KHSO$_4$. The aqueous phase was extracted with chloroform/2-propanol (80:20). The combined organic phases were washed with sat. NaHCO$_3$ and brine, dried over Na$_2$SO$_4$ and concentrated in vacuo. The residue was purified by flash chromatography on silica gel (eluant 5% methanol/chloroform) to give a pale yellow solid identified as 5-(4-cyano-3-methylbenzoyl)-1-methyl-4,10-dihydropyrazolo[5,4-b][1,5]-benzodiazepine (2.4 g, 87%).

15B: 5-(4-Aminomethyl-3-methylbenzoyl)-1-methyl-4,10-dihydropyrazolo[5,4-b][1,5]benzodiazepine

Cobalt(II) chloride hexahydrate (1.59 g, 6.7 mmol) was added to an ice-cold solution of 5-(4-cyano-3-methylbenzoyl)-1-methyl-4,10-dihydropyrazolo[5,4-b][1,5]benzodiazepine (1.15 g, 3.35 mmol) in methanol (35 ml). Sodium borohydride (1.27 g, 33.5 mmol) was added portion wise at 0° C. and the mixture was stirred at RT for 1 h, then quenched with 1M KHSO₄ and concentrated in vacuo. The aqueous residue was diluted with 1M KHSO₄ (40 ml) and filtered through Celite® filter agent. The filtrate was washed with diethyl ether (2×50 ml) then basified with 2 M NaOH and extracted with chloroform. The organic phase was dried over Na₂SO₄ and concentrated in vacuo to give a pale brown solid identified as 5-(4-aminomethyl-3-methylbenzoyl)-1-methyl-4,10-dihydropyrazolo[5,4-b][1,5]benzodiazepine (745 mg, 64%).

15C: 5-(4-(4-(tert-Butyloxycarbonyl)piperazine-1-carbonylaminomethyl)-3-methylbenzoyl)-1-methyl-4,10-dihydropyrazolo[5,4-b][1,5]-benzodiazepine 1,1'-Carbonyldiimidazole (76 mg, 0.47 mmol) was added to a solution of 5-(4-(aminomethyl)-3-methylbenzoyl)-1-methyl-4,10-dihydropyrazolo-[5,4-b][1,5]benzodiazepine (150 mg, 0.43 mmol) and DIEA (0.1 ml, 0.57 mmol) in DMF (10 ml). The solution was stirred for 30 min, tert-butyl piperazine-1-carboxylate (91 mg, 0.49 mmol) was added and stirring was continued for 72 h. The mixture was concentrated in vacuo and the residue was taken up in chloroform. The solution was washed with water and brine, dried and concentrated in vacuo. The residue was purified by flash chromatography on silica gel (eluant 100% EtOAc then 10% methanol/EtOAc) to give a white solid identified as 5-(4-(4-(tert-butyloxycarbonyl)piperazine-1-carbonylaminomethyl)-3-methylbenzoyl)-1-methyl-4,10-dihydropyrazolo[5,4-b][1,5]-benzodiazepine (160 mg, 66%).

15D: 1-Methyl-5-(3-methyl-4-(piperazine-1-carbonylaminomethyl)benzoyl)-4,10-dihydropyrazolo[5,4-b][1,5]benzodiazepine hydrochloride A solution of 5-(4-(4-(tert-butyloxycarbonyl)piperazine-1-carbonylaminomethyl)-3-methylbenzoyl)-1-methyl-4,10-dihydropyrazolo[5,4-b][1,5]benzodiazepine (160 mg, 0.29 mmol) in 4N HCl/dioxan (15 ml) was stirred at room temperature for 30 min then concentrated in vacuo. The residue was azeotroped with diethyl ether to give a white solid identified as 1-methyl-5-(3-methyl-4-(piperazine-1-carbonylaminomethyl)-benzoyl)-4,10-dihydropyrazolo[5,4-b][1,5] hydrochloride (130 mg, 90%).

15E: 5-(4-(4-Cyclopropylmethylpiperazine-1-carbonylaminomethyl)-3-methylbenzoyl)-1-methyl-4,10-dihydropyrazolo[5,4-b][1,5]benzodiazepine To a solution of 1-methyl-5-(3-methyl-4-(piperazine-1-carbonylaminomethyl)-benzoyl)-4,10-dihydropyrazolo[5,4-b][1,5]-benzodiazepine hydrochloride (100 mg, 0.20 mmol) and triethylamine (0.5 ml, 3.59 mmol) in THF (10 ml) were added cyclopropanecarboxaldehyde (14 mg, 0.20 mmol) and sodium cyanoborohydride (15 mg, 0.24 mmol) and the resulting mixture was stirred at room temperature for 24 h then concentrated in vacuo. The residue was dissolved in ethyl acetate and the resulting solution was washed with saturated NaHCO₃, water and brine, dried and concentrated in vacuo. The residue was purified by flash chromatography on silica gel (eluant 10% methanol/EtOAc) to give a white solid identified as 5-(4-(4-cyclopropylmethylpiperazine-1-carbonylaminomethyl)-3-methylbenzoyl)-1-methyl-4,10-dihydropyrazolo[5,4-b][1,5]benzodiazepine (35 mg, 35%).

¹H NMR: d₄-MeOH δ 0.14 (2H, q, J=4.7 Hz), 0.51-0.59 (2H, m), 0.82-0.95 (1H, m), 2.15 (3H, s), 2.28 (2H, d, J=6.7 Hz), 2.52 (4H, t, J=4.9 Hz), 3.43 (4H, t, J=4.9 Hz), 3.80 (3H, s), 3.95 (1H, d, J=14.4 Hz), 4.23 (2H, s), 5.78 (1H, d, J=14.6 Hz), 6.61-6.74 (2H, m), 6.99 (2H, s), 7.03 (1H, s), 7.05-7.14 (1H, m), 7.19-7.24 (2H, m) ppm. MS: [M+H]⁺=514.3

Example 16

5-(4-(4-Benzylpiperazine-1-carbonylaminomethyl)-3-methylbenzoyl)-1-methyl-4,10-dihydropyrazolo[5,4-b][1,5]benzodiazepine

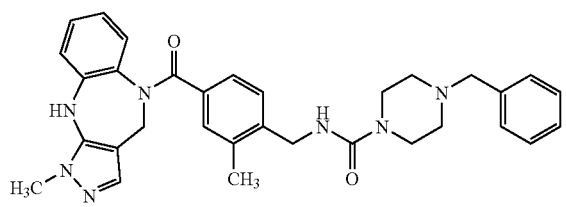

To a solution of 1-methyl-5-(3-methyl-4-(piperazine-1-carbonylaminomethyl)-benzoyl)-4,10-dihydropyrazolo[5,4-b][1,5]hydrochloride (100 mg, 0.20 mmol) and triethylamine (0.5 ml, 3.59 mmol) in THF (10 ml) were added benzaldehyde (21 mg, 0.20 mmol) and sodium cyanoborohydride (15 mg, 0.24 mmol) and the resulting mixture was stirred at room temperature for 24 h then concentrated in vacuo. The residue was dissolved in ethyl acetate and the resulting solution was washed with saturated NaHCO₃, water and brine, dried and concentrated in vacuo. The residue was purified by flash chromatography on silica gel (eluant 5% methanol/EtOAc) to give a white solid identified as 5-(4-(4-benzylpiperazine-1-carbonylaminomethyl)-3-methylbenzoyl)-1-methyl-4,10-dihydropyrazolo[5,4-b][1,5]benzodiazepine (37 mg, 34%).

¹H NMR; δ 2.10 (3H, s), 2.36-2.48 (4H, m), 3.29-3.44 (4H, m), 3.48-3.51 (2H, m), 3.76 (3H, s), 3.96 (1H, d, J=14.6 Hz), 4.22-4.28 (2H, m), 4.61-4.68 (1H, m), 5.88 (1H, d, J=14.6 Hz), 6.46 (1H, s,) 6.62-6.74 (2H, m), 6.82-6.96 (3H, m), 6.98-7.11 (2H, m), 7.19-7.34 (5H, m) ppm. MS: [M+H]⁺=550.2

Example 17

5-(4-(4-(3-Hydroxybenzyl)piperazine-1-carbonylaminomethyl)-3-methylbenzoyl)-1-methyl-4,10-dihydropyrazolo[5,4-b][1,5]benzodiazepine

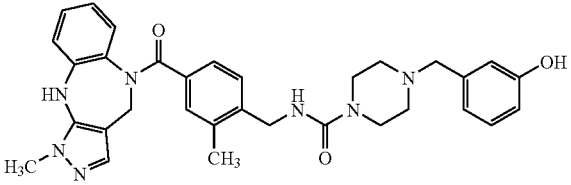

17A: 3-(tert-Butyldimethylsilyloxy)toluene tert-Butyldimethylsilyl chloride (3.00 g, 22.00 mmol) was added to a solution of m-cresol (2.00 g, 18.00 mmol) and triethylamine (4 ml, 28.7 mmol) in dichloromethane (50 ml) at 0° C. The mixture was stirred at room temperature for 24 h then concentrated in vacuo. The residue was purified by flash chromatography on silica gel (eluant 10% EtOAc/pet. ether) to give a colourless oil identified as 3-(tert-butyldimethylsilyloxy)toluene (3.60 g, 88%).

17B: 3-(tert-Butyldimethylsilyloxy)benzyl bromide

N-Bromosuccinimide (2.90 g, 16.20 mmol) and AIBN (266 mg, 1.62 mmol) were added to a stirred solution of 3-(tert-butyldimethylsilyloxy)toluene (3.60 g, 16.20 mmol) in carbon tetrachloride (120 ml) and the mixture was heated at reflux for 24 h, then allowed to cool to room temperature and concentrated in vacuo. The residue was purified by flash chromatography on silica gel (eluant cyclohexane) to give a colourless oil identified as 3-(tert-butyldimethylsilyloxy) benzyl bromide (2.45 g, 50%).

17C: tert-Butyl 4-(3-hydroxybenzyl)piperazine-1-carboxylate

Sodium hydride (406 mg, 60% dispersion in oil, 10.15 mmol) was added portionwise to a stirred solution of tert-butyl piperazine-1-carboxylate in DMF (50 ml) at 0° C. The mixture was allowed to warm to room temperature over 1 h, then a solution of 3-(tert-butyldimethylsilyloxy)benzyl bromide (2.44 g, 8.10 mmol) in DMF (10 ml) was added dropwise and the mixture was stirred at room temperature for 24 h. Water was added and the mixture was stirred for 30 min then poured into EtOAc. The organic phase was washed with saturated NaHCO$_3$ and brine, then concentrated in vacuo. The residue was purified by flash chromatography on silica gel (eluant 40% EtOAc/pet. ether) to give a light brown oil identified as tert-butyl 4-(3-hydroxybenzyl)piperazine-1-carboxylate (2.00 g, 84%).

17D: 1-(3-Hydroxybenzyl)piperazine dihydrochloride

A solution of tert-butyl 4-(3-hydroxybenzyl)piperazine-1-carboxylate (1.94 g, 6.60 mmol) in 4N HCl/dioxan (10 ml) was stirred at room temperature for 30 min then concentrated in vacuo. The residue was triturated with diethyl ether to give a white solid identified as 1-(3-hydroxybenzyl)piperazine dihydrochloride (1.10 g, 63%).

17E: 5-(4-(4-(3-Hydroxybenzyl)piperazine-1-carbonylaminomethyl)-3-methylbenzoyl)-1-methyl-4,10-dihydropyrazolo[5,4-b][1,5]benzodiazepine 1,1'-Carbonyldiimidazole (15 mg, 0.09 mmol) was added to a stirred solution of 5-(4-(aminomethyl)-3-methylbenzoyl)-1-methyl-4,10-dihydropyrazolo[5,4-b][1,5]benzodiazepine (31 mg, 0.09 mmol) and DIEA (0.1 ml 0.57 mmol) in DMF (5 ml). The solution was stirred for 1 h, 1-(3-hydroxybenzyl)piperazine dihydrochloride (27 mg, 0.10 mmol) was added and stirring was continued at room temperature for 24 h. The mixture was concentrated in vacuo and the residue was taken up in EtOAc. The solution was washed with saturated NaHCO$_3$ and brine, then concentrated in vacuo. The residue was purified by flash chromatography on silica gel (eluant 20% methanol/EtOAc) to give a white solid identified as 5-(4-(4-(3-hydroxybenzyl)piperazine-1-carbonylaminomethyl)-3-methylbenzoyl)-1-methyl-4,10-dihydropyrazolo[5,4-b][1,5]benzodiazepine (45 mg, 90%).

$^1$H NMR: δ 2.15 (3H, s), 2.41 (4H, t, J=4.7 Hz), 3.40 (4H, t, J=4.7 Hz), 3.46 (2H, s), 3.80 (3H, s), 3.97 (1H, d, J=14.6 Hz), 4.22 (2H, s), 4.90 (1H, m), 5.78 (1H, d, J=14.6 Hz), 6.62-6.79 (5H, m), 6.99 (2H, s), 7.03-7.27 (6H, m) ppm. MS: [M+H]$^+$=566.1

Example 18

5-(4-(4-(3-Hydroxymethylbenzyl)piperazine-1-carbonylaminomethyl)-3-methylbenzoyl)-1-methyl-4,10-dihydropyrazolo[5,4-b][1,5]benzodiazepine

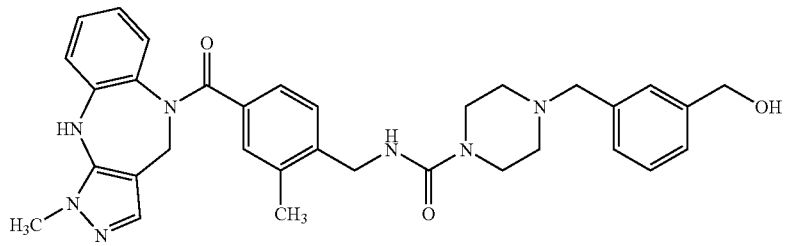

18A: tert-Butyl 4-(3-(methyloxycarbonyl)benzyl)piperazine-1-carboxylate

Methyl 3-(bromomethylbenzoate) (1.23 g, 5.37 mmol) was added to a stirred solution of tert-butyl piperazine-1-carboxylate (1.00 g, 5.37 mmol) and triethylamine (1.50 ml, 10.74 mmol) in dichloromethane (20 ml). The solution was stirred at room temperature for 24 h then concentrated in vacuo. The residue was purified by flash chromatography on silica gel (eluant EtOAc) to give a white solid identified as tert-butyl 4-(3-(methyloxycarbonyl)benzyl)piperazine-1-carboxylate (1.55 g, 86%).

18B: tert-Butyl 4-(3-carboxybenzyl)piperazine-1-carboxylate

Lithium hydroxide monohydrate (339 mg, 9.27 mmol) was added to a solution of tert-butyl 4-(3-(methyloxycarbonyl) benzyl)piperazine-1-carboxylate (1.55 g, 4.63 mmol) in THF (10 ml) and water (2 ml). The solution was stirred at room temperature for 24 h then acidified to pH 5 with 0.3 M KHSO$_4$ and extracted successively with chloroform and dichloromethane. The combined extracts were concentrated in vacuo to give a white solid identified as tert-butyl 4-(3-carboxybenzyl)piperazine-1-carboxylate (1.09 g, 74%).

18C: tert-Butyl 4-(3-(hydroxymethyl)benzyl)piperazine-1-carboxylate

Isobutyl chloroformate (0.47 ml, 3.64 mmol) was slowly added to an ice-cold solution of tert-butyl 4-(3-carboxybenzyl)piperazine-1-carboxylate (1.06 g, 3.31 mmol) and N-methylmorpholine (0.80 ml, 7.28 mmol) in THF (15 ml) The solution was stirred at 0° C. for 45 min and then filtered. The filtrate was added to an ice-cold solution of sodium borohydride (313 mg, 8.27 mmol) in water (10 ml). The stirred mixture was allowed to warm to room temperature over 2 h and then concentrated in vacuo. The residue was taken up in EtOAc and the solution was washed with water and brine then concentrated in vacuo. The residue was purified by flash chromatography on silica gel (eluant EtOAc) to give a white solid identified as tert-butyl 4-(3-(hydroxymethyl)benzyl) piperazine-1-carboxylate (230 mg, 23%).

18D: 1-(3-(Hydroxymethyl)benzyl)piperazine dihydrochloride

A solution of tert-butyl 4-(3-(hydroxymethyl)benzyl)piperazine-1-carboxylate (230 mg, 0.75 mmol) in 4N HCl/dioxan (10 ml) was stirred at room temperature for 45 min then concentrated in vacuo. The residue was azeotroped with toluene to give a white solid identified as 1-(3-(hydroxymethyl)benzyl)-piperazine dihydrochloride (158 mg, 75%).

18E: 5-(4-(4-(3-Hydroxymethylbenzyl)piperazine-1-carbonylaminomethyl)-3-methylbenzoyl)-1-methyl-4,10-dihydropyrazolo[5,4-b][1,5]benzodiazepine 1,1'-Carbonyldiimidazole (20 mg, 0.12 mmol) was added to a solution of 5-(4-(aminomethyl)-3-methylbenzoyl)-1-methyl-4,10-dihydropyrazolo-[5,4-b][1,5]benzodiazepine (35 mg, 0.10 mmol) in DMF (3 ml). The solution was stirred for 1 h, a solution of 1-(3-(hydroxymethyl)benzyl)piperazine dihydrochloride (31 mg, 0.11 mmol) and DIEA (54 µl, 0.30 mmol) in DMF (2 ml) was added and the mixture was stirred at room temperature for 24 h then concentrated in vacuo. The residue taken up in chloroform and the solution was washed with brine and concentrated in vacuo. The residue was purified by flash chromatography on silica gel (eluant 7% methanol/chloroform) to give a white solid identified as 5-(4-(4-(3-hydroxymethylbenzyl)piperazine-1-carbonylaminomethyl)-3-methylbenzoyl)-1-methyl-4,10-dihydropyrazolo-[5,4-b][1,5]benzodiazepine (27 mg, 50%).

¹H NMR: δ 2.00 (3H, s), 2.32-2.36 (4H, m), 3.32-3.45 (4H, m), 3.46 (2H, s), 3.63 (3H, s), 3.91 (1H, d, J=14.6 Hz), 4.10-4.20 (1H, m), 4.66 (2H, s), 5.28-5.29 (1H, m), 5.80 (1H, d, 3=14.3 Hz), 6.50-7.30 (15H, m) ppm. MS: [M+H]⁺=580.3

Example 19

1-Methyl-5-(3-methyl-4-(4-(4-picolyl)piperazine-1-carbonylaminomethyl)benzoyl)-4,10-dihydropyrazolo[5,4-b][1,5]benzodiazepine

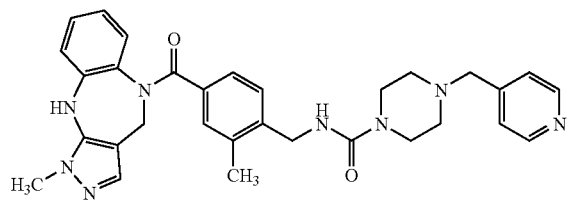

To a solution of 1-methyl-5-(3-methyl-4-(piperazine-1-carbonylaminomethyl)-benzoyl)-4,10-dihydropyrazolo[5,4-b][1,5]hydrochloride (100 mg, 0.20 mmol) and triethylamine (0.5 ml, 3.59 mmol) in THF (10 ml) were added 4-pyridinecarboxaldehyde (21 mg, 0.20 mmol) and sodium cyanoborohydride (15 mg, 0.24 mmol) and the resulting mixture was stirred at room temperature for 24 h then concentrated in vacuo. The residue was dissolved in ethyl acetate and the resulting solution was washed with saturated NaHCO₃, water and brine, dried and concentrated in vacuo. The residue was purified by flash chromatography on silica gel (eluant 10%-30% methanol/EtOAc) to give a white solid identified as 1-methyl-5-(3-methyl-4-(4-(4-picolyl)piperazine-1-carbonylaminomethyl)benzoyl)-4,10-dihydropyrazolo[5,4-b][1,5]benzodiazepine (33 mg, 30%).

¹H NMR: δ 2.13 (3H, s), 2.34-2.49 (4H, m), 3.29-3.47 (4H, m), 3.76 (3H, s), 3.96 (1H, d, J=14.8 Hz), 4.25-4.27 (2H, d, J=4.7 Hz), 4.50-4.60 (1H, m), 5.90 (1H, d, J=14.4 Hz), 6.25 (1H, s), 6.63-6.71 (2H, m), 6.84 (2H, s), 6.92 (1H, s), 7.00-7.12 (2H, m), 7.25 (5H, s), 8.53 (2H, d, J=5.9 Hz) ppm. MS: [M+H]⁺=551.1

Example 20

5-(4-(4-(2-Hydroxyethyl)piperazine-1-carbonylaminomethyl)-3-methylbenzoyl)-1-methyl-4,10-dihydropyrazolo[5,4-b][1,5]benzodiazepine

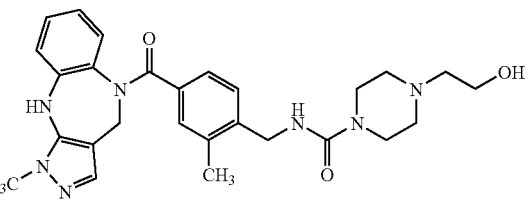

1,1'-Carbonyldiimidazole (20 mg, 0.19 mmol) was added to a solution of 5-(4-(aminomethyl)-3-methylbenzoyl)-1-methyl-4,10-dihydropyrazolo-[5,4-b][1,5]benzodiazepine (31 mg, 0.09 mmol) in DMF (3 ml). The solution was stirred at room temperature for 1 h, a solution of 1-(2-hydroxyethyl)piperazine (13 mg, 0.10 mmol) in DMF (2 ml) was added and stirring was continued for 72 h. The solution was concentrated in vacuo and the residue was partitioned between chloroform and brine. The organic layer was separated and concentrated in vacuo. The residue was purified by flash chromatography on silica gel (eluant 7% methanol/chloroform) to give a white solid identified as 5-(4-(4-(2-hydroxyethyl)piperazine-1-carbonylaminomethyl)-3-methylbenzoyl)-1-methyl-4,10-dihydropyrazolo[5,4-b][1,5](22 mg, 48%).

¹H NMR: δ 2.09 (3H, s), 2.42-2.59 (6H, m), 2.91-3.01 (1H, m), 3.33-3.62 (6H, m), 3.67 (3H, s), 3.93-3.98 (1H, m), 4.20-4.23 (2H, m), 5.00-5.03 (1H, m), 5.84-5.90 (1H, m), 6.64-7.25 (9H, m) ppm. MS: [M+H]⁺=504.2

Example 21

1-Methyl-5-(3-methyl-4-(4-(3-(methylthio)propyl)piperazine-1-carbonylaminomethyl)benzoyl)-4,10-dihydropyrazolo[5,4-b][1,5]benzodiazepine

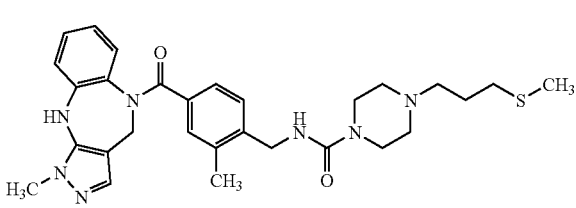

To a solution of 1-methyl-5-(3-methyl-4-(piperazine-1-carbonylaminomethyl)-benzoyl)-4,10-dihydropyrazolo[5,4-b][1,5]hydrochloride (100 mg, 0.20 mmol) and triethylamine (0.5 ml, 3.59 mmol) in THF (10 ml) were added 3-(methylthio)propionaldehyde (21 mg, 0.20 mmol) and sodium cyanoborohydride (15 mg, 0.24 mmol) and the resulting mixture was stirred at room temperature for 24 h then concentrated in vacuo. The residue was dissolved in ethyl acetate and the resulting solution was washed with saturated NaHCO₃, water and brine, dried and concentrated in vacuo. The residue was purified by flash chromatography on silica gel (eluant 20% methanol/EtOAc) to give a white solid identified as 1-methyl-5-(3-methyl-4-(4-(3-(methylthio)propyl)piperazine-1-carbonylaminomethyl)benzoyl)-4,10-dihydropyrazolo[5,4-b][1,5]benzodiazepine (41 mg, 38%).

$^1$H NMR: δ 1.63-1.80 (3H, m), 2.04-2.12 (4H, m), 2.33-2.42 (6H, m), 2.48 (2H, t, J=6.7 Hz), 3.29-3.39 (4H, m), 3.71 (3H, s), 3.93 (1H, d, J=14.4 Hz), 4.12-4.30 (2H, m), 4.57-4.70 (1H, m), 5.85 (1H, d, J=14.6 Hz), 6.44 (1H, s), 6.59-6.71 (2H, m), 6.83-6.88 (2H, m), 6.92-7.08 (2H, m), 7.14-7.27 (2H, m) ppm. MS: [M+H]$^+$=548.0

Example 22

5-(4-(4-(2-Aminoethyl)piperazine-1-carbonylaminomethyl)-3-methylbenzoyl)-1-methyl-4,10-dihydropyrazolo[5,4-b][1,5]dihydrochloride

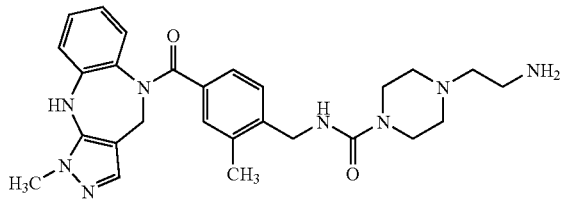

22A: Benzyl 4-(2-hydroxyethyl)piperazine-1-carboxylate

Benzyl chloroformate (3.40 ml, 24.00 mmol) was slowly added to an ice-cold stirred solution of 1-(2-hydroxyethyl)piperazine (2.60 g, 20.00 mmol) and DIEA (7.0 ml, 40.0 mmol) in dichloromethane (75 ml). The mixture was allowed to warm to room temperature and stirred for 24 h then concentrated in vacuo. The residue was purified by flash chromatography on silica gel (eluant 6% methanol/chloroform) to give a colourless gum identified as benzyl 4-(2-hydroxyethyl)piperazine-1-carboxylate (4.80 g, 91%).

22B: Benzyl 4-(2-bromoethyl)piperazine-1-carboxylate

Carbon tetrabromide (7.23 g, 21.80 mmol) was added to an ice-cold stirred solution of benzyl 4-(2-hydroxyethyl)piperazine-1-carboxylate (4.80 g, 18.20 mmol) in dichloromethane (50 ml). The solution was stirred for 5 min, triphenylphosphine (5.95 g, 22.70 mmol) was added, and the mixture was allowed to warm to room temperature and stirred for 3 h. Silica gel was added and the solvent was removed in vacuo. The residue was purified by flash chromatography on silica gel (eluant 50% EtOAc/pet. ether) to give a colourless gum identified as benzyl 4-(2-bromoethyl)piperazine-1-carboxylate (3.45 g, 58%).

22C: Benzyl 4-(2-(tert-butyloxycarbonylamino)ethyl)piperazine-1-carboxylate

Benzyl 4-(2-bromoethyl)piperazine-1'-carboxylate (3.45 g, 10.55 mmol) was added to an ice-cold saturated solution of ammonia in ethanol (60 ml). The mixture was allowed to warm to room temperature and stirred for 4 h, then concentrated in vacuo. The residue was triturated with diethyl ether. The resultant solid was suspended in dichloromethane (75 ml) and triethylamine (2.25 ml, 16.00 mmol). The suspension was cooled to 0° C. and di-tert-butyl dicarbonate (2.40 g, 11.00 mmol) was added. The mixture was allowed to warm to room temperature and stirred for 24 h then concentrated in vacuo. The residue was taken up in EtOAc. The solution was washed with saturated NaHCO$_3$ and brine, then concentrated in vacuo. The residue was purified by flash chromatography on silica gel (eluant 3% methanol/chloroform) to give a yellow gum identified as benzyl 4-(2-(tert-butyloxycarbonylamino)ethyl)piperazine-1-carboxylate (2.60 g, 68%).

22D: tert-Butyl 2-(1-piperazinyl)ethylcarbamate

Hydrogen was passed through a degassed solution of benzyl 4-(2-(tert-butyloxycarbonylamino)ethyl)piperazine-1-carboxylate (2.60 g, 7.16 mmol) in methanol (50 ml) containing 10% palladium on carbon (500 mg) for 2 h. The reaction mixture was filtered through Celite® and the filtrate was concentrated in vacuo to give a yellow gum identified as tert-butyl 2-(1-piperazinyl)ethyl-carbamate (1.60 g, 97%).

22E: 5-(4-(4-(2-(tert-Butyloxycarbonylaminoethyl)piperazine-1-carbonylaminomethyl)-3-methylbenzoyl)-1-methyl-4,10-dihydropyrazolo-[5,4-b][1,5]benzodiazepine 1,1'-Carbonyldiimidazole (25 mg, 0.15 mmol) was added to a solution of 5-(4-(aminomethyl)-3-methylbenzoyl)-1-methyl-4,10-dihydropyrazolo-[5,4-b][1,5]benzodiazepine (31 mg, 0.09 mmol) and DIEA (0.1 ml, 0.57 mmol) in DMF (5 ml). The solution was stirred for 1 h, tert-butyl 2-(1-piperazinyl)-ethylcarbamate (22 mg, 0.10 mmol) was added and stirring was continued at room temperature for 24 h. The mixture was concentrated in vacuo and the residue was taken up in EtOAc. The solution was washed with saturated NaHCO$_3$ and brine, then concentrated in vacuo. The residue was purified by flash chromatography on silica gel (eluant 20% methanol/EtOAc) to give a white solid identified as 5-(4-(4-(2-(tert-butyloxycarbonylaminoethyl)piperazine-1-carbonylaminomethyl)-3-methylbenzoyl)-1-methyl-4,10-dihydropyrazolo, [5,4-b][1,5]benzodiazepine (44 mg, 81%).

22F: 5-(4-(4-(2-Aminoethyl)piperazine-1-carbonylaminomethyl)-3-methylbenzoyl)-1-methyl-4,10-dihydropyrazolo[5,4-b][1,5]dihydrochloride A solution of 5-(4-(4-(2-(tert-butyloxycarbonylaminomethyl)piperazine-1-carbonylaminomethyl)-3-methylbenzoyl)-1-methyl-4,10-dihydropyrazolo-[5,4-b][1,5]benzodiazepine (42 mg, 0.07 mmol) in 4N HCl/dioxan (5 ml) was stirred at room temperature for 30 min then concentrated in vacuo. The residue was dissolved in acetonitrile/water and lyophilised to give a white solid identified as 5-(4-(4-(2-aminoethyl)piperazine-1-carbonylaminomethyl)-3-methylbenzoyl)-1-methyl-4,10-dihydropyrazolo[5,4-b][1,5]dihydrochloride (37 mg, 92%).

$^1$H NMR: δ 2.17 (3H, s), 3.30-3.35 (4H, m), 3.41-3.50 (1H, m), 3.56-3.72 (4H, m), 4.00 (3H, s), 4.04 (1H, s), 4.26 (2H, s), 4.83-4.89 (2H, m), 5.88 (1H, d, J=15 Hz), 6.83-6.84 (2H, m), 6.92-7.13 (4H, m), 7.15-7.28 (1H, m), 7.36 (1H, d, J=7.9 Hz), 7.96 (1H, s) ppm. MS: [M+H]$^+$=503.5

Example 23

1-Methyl-5-(3-methyl-4-(4-methylperhydro-1,4-diazepine-1-carbonylaminomethyl)benzoyl)-4,10-dihydropyrazolo[5,4-b][1,5]benzodiazepine

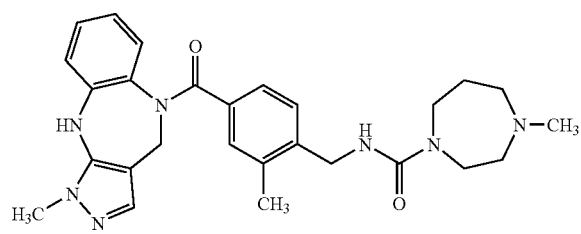

1,1'-Carbonyldiimidazole (37 mg, 0.23 mmol) was added to a solution of 5-(4-(aminomethyl)-3-methylbenzoyl)-1-methyl-4,10-dihydropyrazolo-[5,4-b][1,5]benzodiazepine (75 mg, 0.22 mmol) in DMF (2 ml). The solution was stirred for 1 h, a solution of 1-methylhomopiperazine (27 mg, 0.24 mmol) and DIEA (31 mg, 0.24 mmol) in DMF (1 ml) was added and stirring was continued for 24 h. The mixture was concentrated in vacuo and the residue was purified by chromatography on silica gel (eluant 30/2/1-1/1/1 chloroform/methanol/concentrated ammonia) to give a white solid identified as 1-methyl-5-(3-methyl-4-(4-methylperhydro-1,4-diazepine-1-carbonylaminomethyl)benzoyl)-4,10-dihydropyrazolo[5,4-b][1,5](38 mg, 36%).

$^1$H NMR: δ 1.80-1.99 (2H, m), 2.10 (3H, s), 2.35 (3H, s), 2.51-2.69 (4H, m), 3.39 (2H, t, J=5.9 Hz), 3.45-3.68 (2H, m), 3.63 (3H, s), 3.95 (1H, d, J=14.6 Hz), 4.23 (2H, t, J=4.2 Hz), 4.65-4.75 (1H, m), 5.85 (1H, d, J=14.6 Hz), 6.65-6.75 (2H, m), 6.76-6.88 (2H, m), 6.90-7.09 (2H, m), 7.11-7.22 (2H, m) ppm. MS: [M+H]$^+$=488.2

Example 24

5-(4-(4-(2-Hydroxyethyl)piperazine-1-carbonylaminomethyl)-3-methylbenzoyl)-1-methyl-4,10-dihydropyrazolo[4,5-c]pyrido[2,3-b][1,4]diazepine

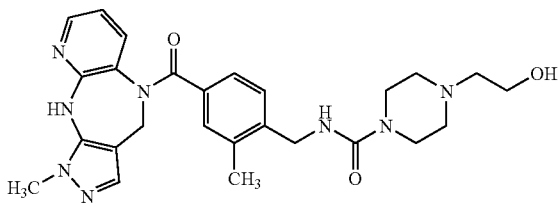

24A: 5-(4-Cyano-3-methylbenzoyl)-1-methyl-4,10-dihydropyrazolo[4,5-c]pyrido[2,3-b][1,4]diazepine Thionyl chloride (0.6 ml, 9.00 mmol) was added to a suspension of 4-cyano-3-methylbenzoic acid (322 mg, 2.00 mmol) in toluene (10 ml). The mixture was heated at reflux for 2 h, allowed to cool and concentrated in vacuo. The residue was azeotroped with toluene and then taken up in dichloromethane (5 ml). The solution was added slowly to a stirred solution of 1-methyl-4,10-dihydropyrazolo[4,5-c]pyrido[2,3-b][1,4]diazepine (400 mg, 2.00 mmol) and triethylamine (0.35 ml, 2.50 mmol) in dichloromethane (5 ml). The mixture was stirred at room temperature for 24 h then concentrated in vacuo. The residue was purified by flash chromatography on silica gel (eluant 5% methanol/chloroform) to give an orange solid identified as 5-(4-cyano-3-methylbenzoyl)-1-methyl-4,10-dihydropyrazolo[4,5-c]pyrido[2,3-b][1,4]diazepine (500 mg, 73%).

24B: 5-(4-Aminomethyl-3-methylbenzoyl)-1-methyl-4,10-dihydropyrazolo[4,5-c]pyrido[2,3-b][1,4]diazepine Cobalt(II) chloride hexahydrate (690 mg, 2.90 mmol) was added to an ice-cold stirred solution of 5-(4-cyano-3-methylbenzoyl)-1-methyl-4,10-dihydropyrazolo[4,5-c]pyrido[2,3-b][1,4]diazepine (500 mg, 1.45 mmol) in methanol (15 nm). Sodium borohydride (570 mg, 15.00 mmol) was added portion wise and the mixture was stirred at room temperature for 1 h 1M KHSO$_4$ was added, the methanol was removed in vacuo, and the aqueous residue was filtered through Celite®. The filtrate was washed with diethyl ether, basified to pH12 with 2M sodium hydroxide and extracted with chloroform. The chloroform extracts were washed with brine and concentrated in vacuo to give a pale orange solid identified as 5-(4-aminomethyl-3-methylbenzoyl)-1-methyl-4,10-dihydropyrazolo[4,5-c]pyrido[2,3-b][1,4]diazepine (400 mg, 79%).

24C: 5-(4-(4-(2-Hydroxyethyl)piperazine-1-carbonylaminomethyl)-3-methylbenzoyl)-1-methyl-4,10-dihydropyrazolo[4,5-c]pyrido[2,3-b][1,4]diazepine 1,1'-Carbonyldiimidazole (20 mg, 0.12 mmol) was added to a solution of 5-(4-aminomethyl-3-methylbenzoyl)-1-methyl-4,10-dihydropyrazolo[4,5-c]pyrido[2,3-b][1,4]diazepine (35 mg, 0.10 mmol) in DMF (3 ml). The solution was stirred for 1 h, a solution of 1-(2-hydroxyethylpiperazine (13 mg, 0.10 mmol) and DIEA (18 μl, 0.10 mmol) in DMF (2 ml) was added and the mixture was stirred at room temperature for 24 h then concentrated in vacuo. The residue taken up in chloroform and the solution was washed with brine and concentrated in vacuo. The residue was purified by flash chromatography on silica gel (eluant 7% methanol/chloroform) to give a pale yellow solid identified as 5-(4-(4-(2-hydroxyethyl)piperazine-1-carbonylaminomethyl)-3-methylbenzoyl)-1-methyl-4,10-dihydropyrazolo[4,5-c]pyrido[2,3-b][1,4]diazepine (29 mg, 58%).

$^1$H NMR: δ 2.42 (3H, br s), 2.44-2.60 (7H, m), 3.20-3.40 (4H, m), 3.55-3.65 (2H, m), 3.79 (3H, s), 3.85-4.00 (1H, m), 4.26 (2H, br s), 4.88 (1H, br s), 5.80-5.95 (1H, m), 6.60 (1H, br s), 6.80-7.30 (6H, m), 8.00 (1H, s) ppm. MS: [M+H]$^+$=505.2

Example 25

4-(2-Cyclopropyl-ethyl)-piperazine-1-carboxylic acid 3-methyl-4-(3-methyl-4,10-dihydro-3H-2,3,4,9-tetraaza-benzo[f]azulene-9-carbonyl)-benzylamide

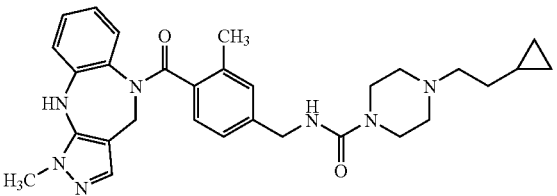

25A: 3-Methyl-4-(3-methyl-4,10-dihydro-3H-2,3,4,9-tetraaza-benzo[f]azulene-9-carbonyl)-benzonitrile Thionyl chloride (0.8 ml, 11.00 mmol) was added to a suspension of 4-Cyano-2-methylbenzoic acid (630 mg, 3.91 mmol) in toluene (30 ml). The mixture was heated at reflux for 2 h, allowed to cool and concentrated in vacuo. The residue was azeotroped with toluene and then taken up in dichloromethane (25 ml). The resulting solution was added to a stirred solution of 1-methyl-4,10-dihydropyrazolo[5,4-b][1,5]benzodiazepine (706 mg, 3.53 mmol) and triethylamine (0.70 ml, 5.02 mmol) in dichloromethane (25 ml). The mixture was heated at reflux for 18 h and cooled. The mixture was diluted with dichloromethane and washed with 0.3 M KHSO$_4$, saturated NaHCO$_3$ and brine then concentrated in vacuo. The residue was purified by flash chromatography on silica gel (eluant ethyl acetate) to give an off-white solid identified as 3-methyl-4-(3-methyl-4,10-dihydro-3H-2,3,4,9-tetraaza-benzo[f]azulene-9-carbonyl)-benzonitrile (1.06 g, 87%).

25B: (4-Aminomethyl-2-methyl-phenyl)-(3-methyl-4,10-dihydro-3H-2,3,4,9-tetraaza-benzolf]azulen-9-yl)-methanone Cobalt(II) chloride hexahydrate (1.45 g, 6.09 mmol) was added to a stirred solution of 3-methyl-4-(3-methyl-4,10- dihydro-3H-2,3,4,9-tetraaza-benzo[f]azulene-9-carbonyl)-benzonitrile (1.04 g, 3.03 mmol) in methanol (50 ml). Sodium borohydride (1.16 g, 30.66 mmol) was added portion-wise and the mixture was stirred at room temperature for 3 h. 0.3 M KHSO₄ was added and the mixture was concentrated in vacuo. The residue was diluted with saturated NaHCO₃ and extracted with chloroform. The chloroform extracts were washed with brine, concentrated in vacuo and freeze dried to give an off-white solid identified as (4-aminomethyl 2-methyl-phenyl)-(3-methyl-4,10-dihydro-3H-2,3,4,9-tetraaza-benzo[f]azulen-9-yl)-methanone (475 mg, 45%).

25C: 4-(2-Cyclopropyl-ethyl)-piperazine-1-carboxylic acid 3-methyl-4-(3-methyl-4,10-dihydro-3H-2,3,4,9-tetraaza-benzo[f]azulene-9-carbonyl)-benzylamide 1,1'-Carbonyldiimidazole (29 mg, 0.18 mmol) was added to a solution of (4-aminomethyl-2-methyl-phenyl)-(3-methyl-4,10-dihydro-3H-2,3,4,9-tetraaza-benzo[f]azulen-9-yl)-methanone (60 mg, 0.17 mmol) in DMF (3 ml). The solution was stirred for 1 h, a solution of 1-(2-Cyclopropyl-ethyl)-piperazine (39 mg, 0.17 mmol) and DIEA (98 µl, 0.55 mmol) in DMF (1 ml) was added and the mixture was stirred at room temperature for 18 h. The mixture was diluted with ethyl acetate and washed with 5% KHCO₃, water and brine and concentrated in vacuo. The residue was purified by flash chromatography on silica gel (eluant 100/10/1 chloroform/methanol/concentrated ammonia) to give a white solid identified as 4-(2-cyclopropyl-ethyl)-piperazine-1-carboxylic acid 3-methyl-4-(3-methyl-4,10-dihydro-3H-2,3,4,9-tetraaza-benzo[f]azulene-9-carbonyl)-benzylamide (51 mg, 56%).

¹H NMR: δ 0.01-0.09 (2H, m) 0.42-0.44 (2H, m), 0.62-0.66 (1H, m), 1.34-1.40 (2H, m), 2.29 (3H, s) 2.31-2.42 (6H, m), 3.31-3.35 (4H, m), 3.66 (3H, s), 3.97 (1H, d, J=14.6 Hz), 4.20 (2H, d, J=5.4 Hz), 4.39-4.41 (1H, m), 4.89-4.94 (1H, m), 5.83 (1H, d, J=14.6 Hz) 6.56-7.26 (8H, m) MS: [M+H]⁺= 528.7

Examples 26-150

The following compounds were prepared using methods analogous to those described above.

Examples 26-35

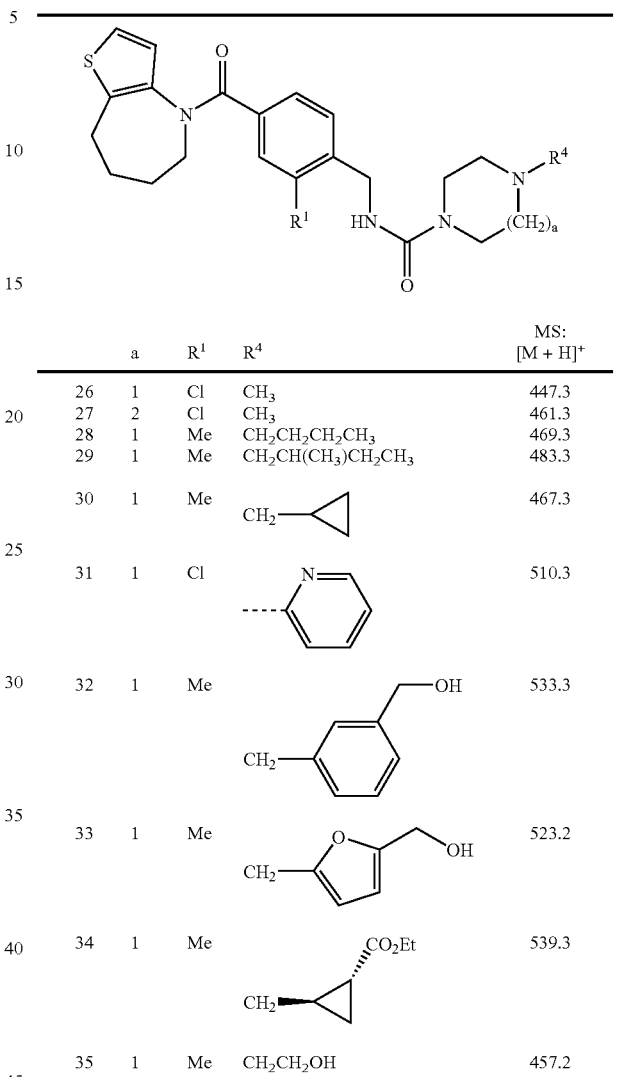

| | a | R¹ | R⁴ | MS: [M + H]⁺ |
|---|---|---|---|---|
| 26 | 1 | Cl | CH₃ | 447.3 |
| 27 | 2 | Cl | CH₃ | 461.3 |
| 28 | 1 | Me | CH₂CH₂CH₂CH₃ | 469.3 |
| 29 | 1 | Me | CH₂CH(CH₃)CH₂CH₃ | 483.3 |
| 30 | 1 | Me | CH₂-cyclopropyl | 467.3 |
| 31 | 1 | Cl | 2-pyridyl | 510.3 |
| 32 | 1 | Me | CH₂-(3-hydroxyphenyl) | 533.3 |
| 33 | 1 | Me | CH₂-(5-hydroxymethyl-furan-2-yl) | 523.2 |
| 34 | 1 | Me | CH₂-cyclopropyl-CO₂Et | 539.3 |
| 35 | 1 | Me | CH₂CH₂OH | 457.2 |

Examples 36-51

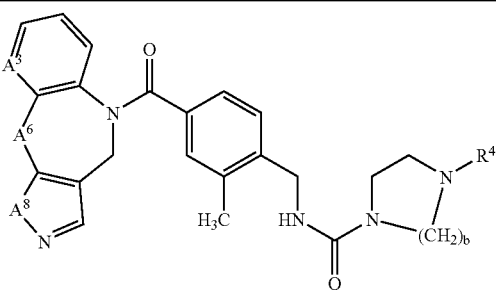

| | A³ | A⁶ | A⁸ | b | R⁴ | MS: [M + H]⁺ |
|---|---|---|---|---|---|---|
| 36 | CH | NH | N—Me | 3 | H | 474.1 |
| 37 | CH | NH | N—Me | 3 | CH₂CH(CH₃)CH₂CH₃ | 544.3 |
| 38 | CH | NH | N—Me | 3 | CH₂C(CH₃)₃ | 544.3 |

-continued
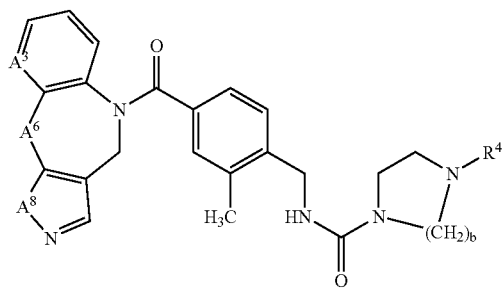
| | A³ | A⁶ | A⁸ | b | R⁴ | MS: [M + H]⁺ |
|---|---|---|---|---|---|---|
| 39 | CH | NH | N—Me | 3 | CH₂–cyclopropyl | 528.3 |
| 40 | CH | N—Me | N—Me | 1 | | 514.3 |
| 41 | N | NH | N—Me | 2 | CH₂–(3-hydroxyphenyl) | 680.2 |
| 42 | CH | N—Me | N—Me | 2 | CH₂–(3-hydroxymethylphenyl) | 594.3 |
| 43 | CH | NH | N—Me | 3 | CH₂–(2-thienyl) | 570.3 |
| 44 | CH | NH | N—Me | 2 | | 556.3 |
| 45 | CH | NH | N—Me | 3 | CH₂–(trans-2-CO₂Et-cyclopropyl) | 600.3 |
| 46 | CH | NH | N—Me | 2 | | 586.3 |
| 47 | N | NH | N—Me | 2 | CH₂CH₂NH₂ | 504.1 |
| 48 | N | NH | N—Me | 2 | CH₂CH₂CH₂NH₂ | 518.3 |
| 49 | CH | NH | N—Me | 2 | CH₂–piperidinyl | 571.4 |
| 50 | N | NH | N—Me | 2 | | 572.3 |
| 51 | CH | NH | N—CH₂Ph | 2 | CH₂CH₂OH | 580.2 |

Examples 52-126

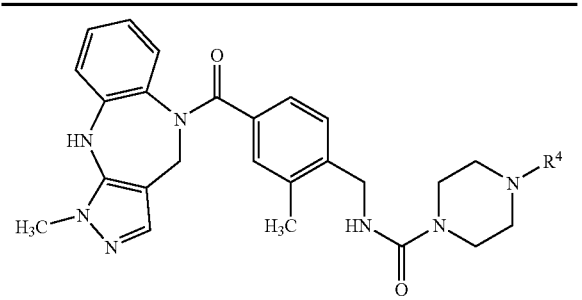

| | R⁴ | MS: [M + H]⁺ |
|---|---|---|
| 52 | H | 460.2 |
| 53 | CH₃ | 474.2 |
| 54 | CH₂CH₃ | 488.2 |
| 55 | CH₂CH₂CH₃ | 502.3 |
| 56 | CH₂CH₂CH₂CH₃ | 516.3 |
| 57 | CH₂CH₂CH₂CH₂CH₃ | 530.3 |
| 58 | CH₂CH₂CH₂CH₂CH₂CH₃ | 544.3 |
| 59 | CH₂CH₂CH(CH₃)₂ | 530.3 |
| 60 | CH₂CH(CH₃)CH₂CH₃ | 530.3 |
| 61 | CH₂CH(CH₂CH₃)₂ | 544.3 |
| 62 | CH₂CH₂C(CH₃)₃ | 544.2 |
| 63 | CH₂-cyclohexyl | 556.3 |
| 64 | CH₂CH=CH₂ | 500.1 |
| 65 | CH₂C(CH₃)=CHCH₃ (prenyl-type) | 528.3 |
| 66 | -phenyl | 536.2 |
| 67 | CH₂-(3-methoxyphenyl) | 580.3 |
| 68 | CH₂-(2-hydroxymethylphenyl) | 580.3 |
| 69 | CH₂-(4-hydroxymethylphenyl) | 580.2 |
| 70 | CH₂-(4-CO₂CH₃-phenyl) | 608.3 |

-continued

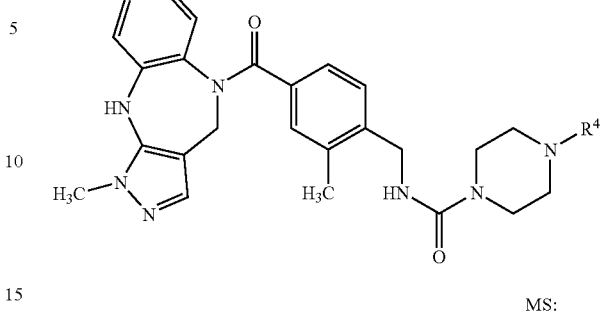

| | R⁴ | MS: [M + H]⁺ |
|---|---|---|
| 71 | CH₂-(2-(1,2,3-thiadiazol-4-yl)phenyl) | 634.2 |
| 72 | CH₂-(3-(1,2,3-thiadiazol-4-yl)phenyl) | 634.2 |
| 73 | CH₂-(4-(1,2,3-thiadiazol-4-yl)phenyl) | 634.2 |
| 74 | CH₂-(furan-2-yl) | 540.3 |
| 75 | CH₂-(5-hydroxymethylfuran-2-yl) | 570.2 |
| 76 | CH₂-(5-CO₂Me-thiophen-2-yl) | 614.2 |
| 77 | CH₂-(5-hydroxymethylthiophen-2-yl) | 586.3 |
| 78 | CH₂-(3-Cl-5-CO₂Me-thiophen-2-yl) | 648.2 |
| 79 | CH₂-(3-Cl-5-hydroxymethylthiophen-2-yl) | 620.2 |

-continued
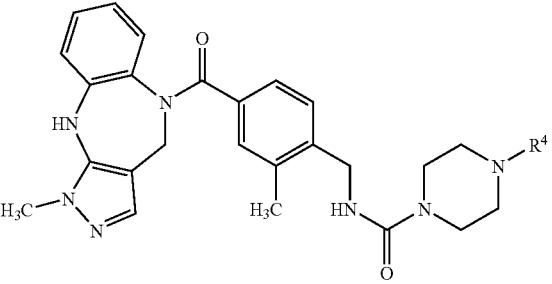
| | R⁴ | MS: [M + H]⁺ |
|---|---|---|
| 80 | 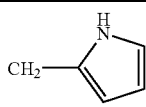 | 538.2 |
| 81 | 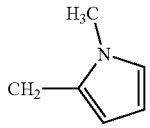 | 553.1 |
| 82 | 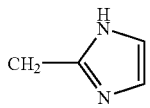 | 540.2 |
| 83 | 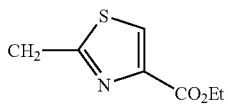 | 629.2 |
| 84 | 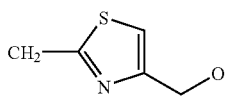 | 587.3 |
| 85 | 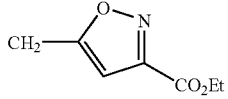 | 599.2 |
| 86 | 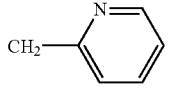 | 551.3 |
| 87 | 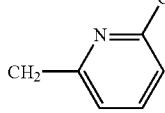 | 609.1 |
| 88 | 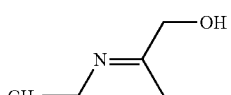 | 581.3 |
| 89 | 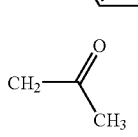 | 516.3 |
-continued
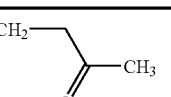
| | R⁴ | MS: [M + H]⁺ |
|---|---|---|
| 90 | 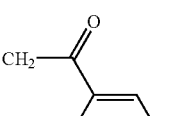 | 530.2 |
| 91 | 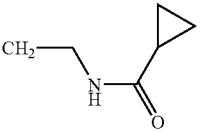 | 592.2 |
| 92 | $CH_2CH_2CO_2CH_3$ | 546.3 |
| 93 | $CH_2CH_2CO_2H$ | 532.1 |
| 94 | $CH_2CH_2CH_2CO_2CH_3$ | 560.2 |
| 95 | $CH_2CH_2CN$ | 513.4 |
| 96 | $CH_2CH_2N_3$ | 529.2 |
| 97 | 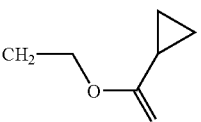 | 571.2 |
| 98 | 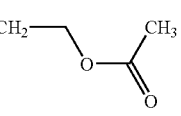 | 572.2 |
| 99 | 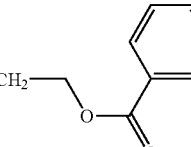 | 546.3 |
| 100 | 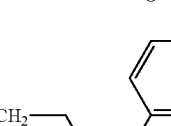 | 608.3 |
| 101 |  | 609.3 |

| | 51 | | | 52 | |
|---|---|---|---|---|---|
| | -continued | | | -continued | |
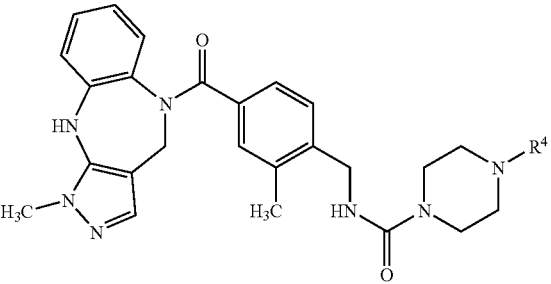
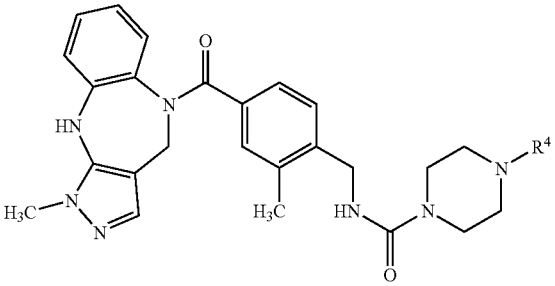
| | R⁴ | MS: [M + H]⁺ | | R⁴ | MS: [M + H]⁺ |
|---|---|---|---|---|---|
| 102 | 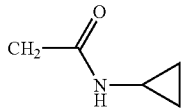 | 557.3 | 114 | 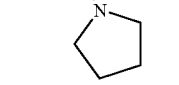 | 536.2 |
| 103 | 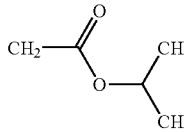 | 560.3 | 115 | 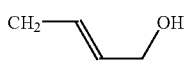 | 534.3 |
| 104 | 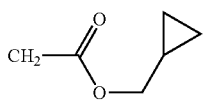 | 572.2 | 116 | 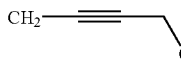 | 548.1 |
| 105 | CH₂CH₂CH₂NH₂ | 517.3 | 117 | 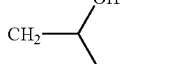 | 576.3 |
| 106 | CH₂CH₂N(CH₂CH₃)₂ | 559.3 | | | |
| 107 | 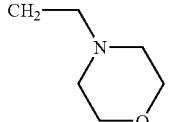 | 573.2 | 118 | CH₂CH₂OCH₃ | 518.2 |
| | | | 119 | CH₂CH₂OCH₂CH₃ | 532.3 |
| | | | 120 | CH₂CH₂OCH₂CH₂OCH₃ | 562.3 |
| | | | 121 | CH₂CH₂OCH₂CH₂OCH₂CH₃ | 576.3 |
| 108 | 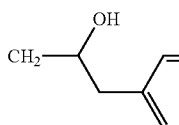 | 557.3 | 122 | | 594.3 |
| 109 | CH₂CH₂CH₂CH₂OH | 532.3 | | | |
| 110 | | 530.2 | 123 | | 528.4 |
| 111 | | 536.9 [M + Na]⁺ | 124 | | 544.4 |
| 112 | | 532.3 | 125 | | 542.6 |
| 113 | | 594.3 | 126 | | 528.7 |

Examples 127-129
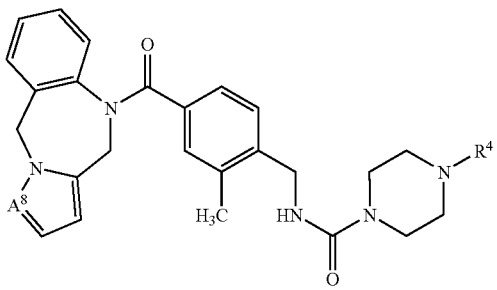
| | $A^8$ | $R^4$ | MS: $[M+H]^+$ |
|---|---|---|---|
| 127 | CH | 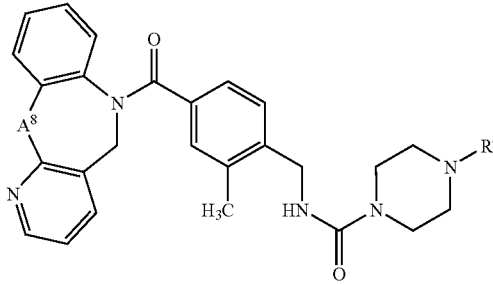 | 550.3 |
| 128 | CH |  | 592.3 |
| 129 | N | $CH_2CH_2OH$ | 489.0 |
Examples 130-137
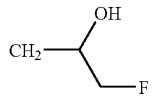
| | $A^6$ | $R^4$ | MS: $[M+H]^+$ |
|---|---|---|---|
| 130 | NH | 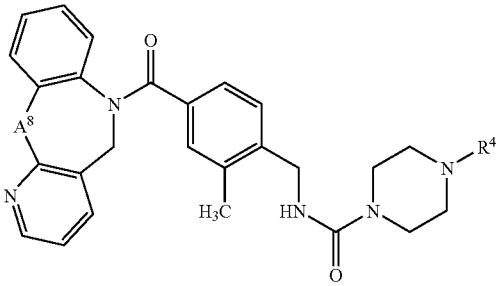 | 584.9 $[M+Na]^+$ |
| 131 | NH | 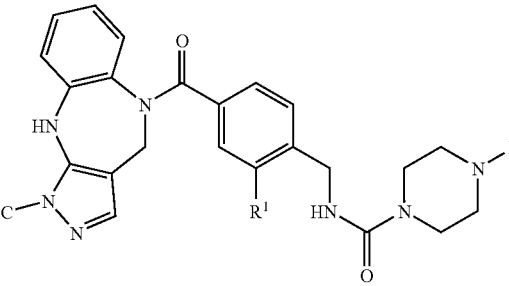 | 513.3 |
| 132 | NH | $CH_2CH_2CH_2NH_2$ | 514.3 |
| 133 | NH | $CH_2CH_2NH_2$ | 500.3 |
| 134 | O | $CH_2CH_2OH$ | 502.1 |
| 135 | NH | $CH_2CH_2OH$ | 501.3 |
-continued
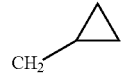
| | $A^6$ | $R^4$ | MS: $[M+H]^+$ |
|---|---|---|---|
| 136 | NH | 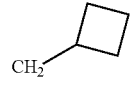 | |
| 137 | NH | 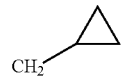 | 533.3 |
Examples 138-141
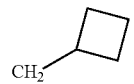
| | $R^1$ | $R^4$ | MS: $[M+H]^+$ |
|---|---|---|---|
| 138 | F |  | 518.5 |
| 139 | F |  | 532.4 |
| 140 | Cl |  | 534.2 |
| 141 | Cl |  | 548.2 |

Examples 142-149

| | R³ | R⁴ | MS: [M + H]⁺ |
|---|---|---|---|
| 142 | CH₃ | CH₂-cyclopropyl | 514.3 |
| 143 | CH₃ | CH₂-cyclobutyl | 528.3 |
| 144 | F | CH₂-cyclopropyl | 518.3 |
| 145 | F | CH₂-cyclobutyl | 532.1 |
| 146 | Cl | CH₂-cyclopropyl | 534.5 |
| 147 | Cl | CH₂-cyclobutyl | 548.6 |
| 148 | CH₂CH₃ | CH₂-cyclopropyl | – |
| 149 | OCH₃ | CH₂-cyclobutyl | 544.4 |

Example 150

| | R⁴ | MS: [M + H]⁺ |
|---|---|---|
| 150 | CH₂-cyclobutyl | 514.3 |

Example 151

In Vitro Testing

Compounds were assayed to determine their ability to inhibit the cellular consequences of AVP stimulation on intact cells. In the assay, the compounds of the invention cause significant inhibition of cellular activation at concentrations of 30 µM or less. Preferred compounds cause significant inhibition at concentrations of 300 nM

Example 152

Tablet for Oral Administration

Tablets containing 100 mg of the compound of Example 15 as the active agent are prepared from the following:

| | |
|---|---|
| Compound of Example 15 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 15.

The forgoing demonstrates that the compounds according to the present invention act as antagonists at the vasopressin $V_{1a}$ receptor and accordingly they may find utility as pharmaceutical agents for the treatment of conditions such as primary dysmenorrhoea, pre-term labour, hypertension, Raynauld's disease, brain oedema, motion sickness, small cell lung cancer, depression, anxiety; hyponatremia, liver cirrhosis and congestive heart failure.

The scope of the present invention is further defined in the following claims.

The invention claimed is:

1. A compound selected from the group consisting of:
   4-(2-Cyclopropyl-ethyl)-piperazine-1-carboxylic acid 2-methyl-4-(3-methyl-4,10-dihydro-3H-2,3,4,9-tetraaza-benzo [f]azulene-9-carbonyl)-benzylamide;
   4-Cyclopropylmethyl-piperazine-1-carboxylic acid 3-methyl-4-(3-methyl-4,10-dihydro-3H-2,3,4,9-tetraaza-benzo [f]azulene-9-carbonyl)-benzylamide;
   4-Cyclopropylmethyl-piperazine-1-carboxylic acid 3-fluoro-4-(3-methyl-4,10-dihydro-3H-2,3,4,9-tetraaza-benzo [f]azulene-9-carbonyl)-benzylamide;
   4-(2-Hydroxymethyl-cyclopropylmethyl)-piperazine-1-carboxylic acid 2-methyl-4-(3-methyl-4,10-dihydro-3H-2,3,4,9-tetraaza-benzo[f]azulene-9-carbonyl)-benzylamide;
   4-Cyclopentylmethyl-piperazine-1-carboxylic acid 2-methyl-4-(3-methyl-4,10-dihydro-3H-2,3,4,9-tetraaza-benzo [f]azulene-9-carbonyl)-benzylamide;
   4-Cyclopropylmethyl-piperazine-1-carboxylic acid 3-chloro-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 3-chloro-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 2-methyl-4-(3-methyl-4,10-dihydro-3H-2,3,4,9-tetraaza-benzo [f]azulene-9-carbonyl)-benzylamide;
   4-(2-Cyclopropyl-ethyl)-piperazine-1-carboxylic acid 3-methyl-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 3-methyl-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 3-fluoro-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 2-fluoro-4-(3-methyl-4,10-dihydro-3H-2,3,4,9-tetraaza-benzo [f]azulene-9-carbonyl)-benzylamide;
   4-Cyclopropylmethyl-piperazine-1-carboxylic acid 2-fluoro-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 4-(3-methyl-4,10-dihydro-3H-2,3,4,9-tetraaza-benzo [f]azulene-9-carbonyl)-benzylamide;
   4-Cyclopropylmethyl-piperazine-1-carboxylic acid 2-ethyl-4-(3-methyl-4,10-dihydro-3H-2,3,4,9-tetraaza-benzo [f]azulene-9-carbonyl)-benzylamide;
   4-Cyclobutylmethyl-piperazine-1-carboxylic acid 2-chloro-4-(3-methyl-4,10-dihydro-3H-2,3,4,9-tetraaza-benzo [f]azulene-9-carbonyl)-benzylamide;
   4-Cyclopropylmethyl-piperazine-1-carboxylic acid 2-chloro-4-(3-methyl-4,10-dihydro-3H-2,3,4,9-tetraaza-benzo[f]azulene-9-carbonyl)-benzylamide; and
   4-Cyclobutylmethyl-piperazine-1-carboxylic acid 3-methoxy-4-(3-methyl-4,10-dihydro-3H-2,3,4,9-tetraaza-benzo [f]azulene-9-carbonyl)-benzylamide,
   or a pharmaceutically acceptable salt thereof.

2. A pharmaceutical composition comprising a compound according to claim 1 as an active agent.

3. A pharmaceutical composition according to claim 2 formulated as a tablet or capsule for oral administration.

4. A pharmaceutical composition according to claim 2, comprising 0.1-1000 mg of said active agent.

5. A pharmaceutical composition according to claim 2, comprising 1-250 mg of said active agent.

6. A method for treatment of male erectile dysfunction which comprises the administration to a person in need of such treatment of therapeutically effective amount of a compound selected from the group consisting of:
   4-(2-Cyclopropyl-ethyl)-piperazine-1-carboxylic acid 2-methyl-4-(3-methyl-4,10-dihydro-3H-2,3,4,9-tetraaza-benzo[f]azulene-9-carbonyl)-benzylamide,
   4-Cyclopropylmethyl-piperazine-1-carboxylic acid 3-methyl-4-(3-methyl-4,10-dihydro-3H-2,3,4,9-tetraaza-benzo[f]azulene-9-carbonyl)-benzylamide,
   4-Cyclopropylmethyl-piperazine-1-carboxylic acid 3-fluoro-4-(3-methyl-4,10-dihydro-3H-2,3,4,9-tetraaza-benzo[f]azulene-9-carbonyl)-benzylamide,
   4-(2-Hydroxymethyl-cyclopropylmethyl)-piperazine-1-carboxylic acid 2-methyl-4-(3-methyl-4,10-dihydro-3H-2,3,4,9-tetraaza-benzo[f]azulene-9-carbonyl)-benzylamide,
   4-Cyclopentylmethyl-piperazine-1-carboxylic acid 2-methyl-4-(3-methyl-4,10-dihydro-3H-2,3,4,9-tetraaza-benzo[f]azulene-9-carbonyl)-benzylamide,
   4-Cyclopropylmethyl-piperazine-1-carboxylic acid 3-chloro-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 3-chloro-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 2-methyl-4-(3-methyl-4,10-dihydro-3H-2,3,4,9-tetraaza-benzo[f]azulene-9-carbonyl)-benzylamide,
   4-(2-Cyclopropyl-ethyl)-piperazine-1-carboxylic acid 3-methyl-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 3-methyl-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 3-fluoro-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 2-fluoro-4-(3-methyl-4,10-dihydro-3H-2,3,4,9-tetraaza-benzo[f]azulene-9-carbonyl)-benzylamide,
   4-Cyclopropylmethyl-piperazine-1-carboxylic acid 2-fluoro-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 4-(3-methyl-4,10-dihydro-3H-2,3,4,9-tetraaza-benzo[f]azulene-9-carbonyl)-benzylamide,
   4-Cyclopropylmethyl-piperazine-1-carboxylic acid 2-ethyl-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 2-chloro-4-(3-methyl-4,10-dihydro-3H-2,3,4,9-tetraaza-benzo[f]azulene-9-carbonyl)-benzylamide,
   4-Cyclopropylmethyl-piperazine-1-carboxylic acid 2-chloro-4-(3-methyl-4,10-dihydro-3H-2,3,4,9-tetraaza-benzo[f]azulene-9-carbonyl)-benzylamide,
   4-Cyclobutylmethyl-piperazine-1-carboxylic acid 3-methoxy-4-(3-methyl-4,10-dihydro-3H-2,3,4,9-tetraaza-benzo[f]azulene-9-carbonyl)-benzylamide; and
   pharmaceutically acceptable salts thereof.

7. A method for treatment of pre-term labor which comprises the administration to a person in need of such treatment of therapeutically effective amount of a compound selected from the group consisting of:
   4-(2-Cyclopropyl-ethyl)-piperazine-1-carboxylic acid 2-methyl-4-(3-methyl-4,10-dihydro-3H-2,3,4,9-tetraaza-benzo[f]azulene-9-carbonyl)-benzylamide, 4-Cyclopropylmethyl-piperazine-1-carboxylic acid 3-methyl-4-(3-methyl-4,10-dihydro-3H-2,3,4,9-tetraaza-benzo[f]azulene-9-carbonyl)-benzylamide, 4-Cyclopropylmethyl-piperazine-1-carboxylic acid 3-fluoro-4-(3-methyl-4,10-dihydro-3H-2,3,4,9-tetraaza-benzo[f]azulene-9-carbonyl)-benzylamide, 4-(2-Hydroxymethyl-cyclopropylmethyl)-piperazine-1-carboxylic acid 2-methyl-4-(3-methyl-4,10-dihydro-3H-2,3,4,9-tetraaza-benzo[f]azulene-9-carbonyl)-benzylamide, 4-Cyclopentylmethyl-piperazine-1-carboxylic acid 2-methyl-4-(3-methyl-4,10-dihydro-3H-2,3,4,9-tetraaza-benzo[f]azulene-9-carbonyl)-benzylamide, 4-Cyclopropylmethyl-piperazine-1-carboxylic acid 3-chloro-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 3-chloro-4-(3-methyl-4,10-dihydro-3H-2,3,4,9-tetraaza-benzol[f]azulene-9-carbonyl)-benzylamide, 4-Cyclobutylmethyl-piperazine-1-carboxylic acid 2-methyl-4-(3-methyl-4,10-dihydro-3H-2,3,4,9-tetraaza-benzo[f]azulene-9-carbonyl)-benzylamide, 4-(2-Cyclopropyl-ethyl)-piperazine-1-carboxylic acid 3-methyl-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 3-methyl-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 3-fluoro-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 2-fluoro-4-(3-methyl-4,10-dihydro-3H-2,3,4,9-tetraaza-benzo[f]azulene-9-carbonyl)-benzylamide, 4-Cyclopropylmethyl-piperazine-1-carboxylic acid 2-fluoro-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 4-(3-methyl-4,10-dihydro-3H-2,3,4,9-tetraaza-benzo[f]azulene-9-carbonyl)-benzylamide, 4-Cyclopropylmethyl-piperazine-1-carboxylic acid 2-ethyl-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 2-chloro-4-(3-methyl-4,10-dihydro-3H-2,3,4,9-tetraaza-benzo[f]azulene-9-carbonyl)-benzylamide, 4-Cyclopropylmethyl-piperazine-1-carboxylic acid 2-chloro-4-(3-methyl-4,10-dihydro-3H-2,3,4,9-tetraaza-benzo[f]azulene-9-carbonyl)-benzylamide, 4-Cyclobutylmethyl-piperazine-1-carboxylic acid 3-methoxy-4-(3-methyl-4,10-dihydro-3H-2,3,4,9-tetraaza-benzo[f]azulene-9-carbonyl)-benzylamide; and pharmaceutically acceptable salts thereof.

\* \* \* \* \*